US005840570A

United States Patent [19]

Berka et al.

[11] Patent Number: 5,840,570
[45] Date of Patent: Nov. 24, 1998

[54] ASPARTIC PROTEINASE DEFICIENT FILAMENTOUS FUNGI

[76] Inventors: Randy M. Berka, 331 W. 27th Ave., San Mateo, Calif. 94403; Kirk J. Hayenga, 1910 Garden Dr. No. 108, Berlingame, Calif. 94010; Virgil B. Lawlis, 1105 Bailwood Way, San Mateo, Calif. 94403; Michael Ward, 381 Myrtle St., Half Moon Bay, Calif. 94019

[21] Appl. No.: 345,018

[22] Filed: Nov. 23, 1994

Related U.S. Application Data

[63] Continuation of Ser. No. 931,123, Aug. 17, 1992, abandoned, which is a continuation of Ser. No. 214,237, Jul. 1, 1988, abandoned.

[51] Int. Cl.$^6$ .............................. C12N 1/15; C12N 15/09; C12N 15/12
[52] U.S. Cl. ................................. 435/254.3; 435/256.1; 435/69.1; 435/71.1; 435/172.3; 435/172.1
[58] Field of Search ................................. 435/69.1, 71.1, 435/91.1, 172.3, 254.3, 256.1, 320.1, 172.1

[56] References Cited

U.S. PATENT DOCUMENTS 4,963,487  10/1990  Schimmel .

FOREIGN PATENT DOCUMENTS

| A-130756 B1 | 9/1985 | European Pat. Off. . |
|---|---|---|
| 0 206783 | 12/1986 | European Pat. Off. . |
| A-0230670 A2 | 5/1987 | European Pat. Off. . |
| 0 244234 | 11/1987 | European Pat. Off. . |
| 0 249 350 | 12/1987 | European Pat. Off. . |
| 0 215594 B1 | 1/1995 | European Pat. Off. . |
| WO 85/03949 | 12/1985 | WIPO . |
| WO 86/01825 | 3/1986 | WIPO . |
| WO 85/05812 | 9/1986 | WIPO . |
| WO 87/04461 | 7/1987 | WIPO . |

OTHER PUBLICATIONS

Mattern et al. (1992) Mol Gen Genet vol. 234: 332–336.
Kusters–van Someren et al. (1991) Curr. Genetics vol. 19: 21–26.
Miller et al., 1985, *Molecular and Cellular Biology*, vol. 5(7):1714–1721.
Barkholt, 1987, *Eur. J. Biochem.* 162: 327–338.
Mellor et al., 1983, *Gene*, 24: 1–14.
Gray et al., 1986, *Gene*, 48:41–53.
Horiuchi et al, 1988 (Jan.), *J. Bacteriol.*, vol. 170(1):272–278.
Cullen et al., 1987, *Bio/Technology*, vol. 5: 369–376.
Van Heeswijck et al., 1985, *Biological Abstracts*, vol. 79(12), Abstract No. 104735.
Ostoslavskaya et al., 1987, *Biological Abstracts*, vol. 83(10), Abstract No. 101239.
Yang et al., 1984, *J Bacteriol.* vol. 160(1):15–21.
Suggs et al., 1981, *PNAS*, vol. 78(11):6613–6617.

Ido, et al. "Substrate Specificity of Acid Proteinase A. from *Aspergillus niger* var. macrosporus", *Agric. Biol. Chem.*, 51 (10), pp. 2855–2856 (1987).
Kay, John., "Aspartic Proteinases and Their Inhibitors," Proceedings of the FEBS Advanced Course No. 84/07, Prague, Czechoslovakia, Aug. 10–24, 1984.
Sodek et al., "Microbial Acid Proteinases," *Methods in Enzymology*, 19, pp. 372–383 (1970).
Sakka et al., "Purification and Some Properties of Serine Proteinase from a Mutant of *Aspergillus niger*," *J. Fement Technol.*, vol. 63, No. 5, 479–483 (1985).
Raper et al., "Identification," *The Genus Aspergillus*, pp. 129–344 (1977).
Berka et al., "The Development of Gene Expression Systems for Filamentous Fungi," *Biotech. Adv.*, vol. 7 pp. 127–154 (1989).
Mäntylä et al., "Cloning of the Aspartic Protease Gene from *Trichoderma Reesei*," ECFG2–Poster presented at the 2nd European Conference on Fungal Genetics at Lunteren, The Netherlands (Apr. 28–May 1, 1994).
Archer et al., "Proteolytic Degradation of Heterologous Proteins Expressed in *Asperillus Niger*," *Biotechnology Letters*, vol. 14, No. 5, pp. 357–362 (1992).
Smith et al., "Characterization of Two Aspartyl Proteinases from a Commercial Fungal (Mucor miehei) Rennet," *Can. Inst. Food Sci. Technol. J.*, vol. 24, No. 1/2, pp. 48–56 (1991).
Langley et al., "Characterization of purified hepatitis B surface antigen containing pre–S(2) epitopes expressed in *Saccharomyces cerevisiae*," *Gene*, vol. 67, No. 2, pp. 229–245 (1988).
Majima et al., "Comparative Study on the Specificities of Several Fungal Aspartic and Acidic Proteinases towards the Tetradecapeptide of a Renin Substrate," *Agric. Biol. Chem.*, vol. 52, No. 3, pp. 787–793 (1988).
Nakatani et al., "Kinetic Study on the Interaction of *Rhizopus chinensis* Aspartic Protease with Streptomyces Pepsin Inhibitor (Acetylpepstatin)," *Archives of Biochemistry and Biophysics*, vol. 263, No. 2, pp. 311–314 (1988).
Finkelstein, "Molecular Genetics of Yeasts and Filamentous Fungi and Its Impact on Biotechnology," 19th Lunteren Lectures on Molecular Genetics, Lunteren, The Netherlands (29 Sep.–2 Oct. 1987).
Mollison et al., "High–level C5a gene expression and recovery of recombinant human C5a from *Escherichia coli*," *Agents and Actions*, vol. 21, No. 3/4, pp. 366–370 (1987).
Fahnestock et al., "Protease–Deficient *Bacillus subtillis* Host Strains for Production of Staphylococcal Protein A," *Appl. Environ. Microbiol.*, vol. 53, No. 2, pp. 379–384 (1987).

(List continued on next page.)

*Primary Examiner*—Jasemine C. Chambers
*Assistant Examiner*—Scott D. Priebe
*Attorney, Agent, or Firm*—Debra J. Glaister

[57] ABSTRACT

This invention relates to novel mutant filamentous fungi which are deficient in the gene for the corresponding aspartic proteinase. These organisms are useful production hosts in the production of heterologous polypeptides such as chymosin.

10 Claims, 11 Drawing Sheets

OTHER PUBLICATIONS

Honjo et al., "Construction of a highly efficient host–vector system for secretion of heterologous protein in *Bacillus subtillis*," *Journal of Biotechnology*, vol. 6, No. 3, pp. 191–204 (1987).

Bott et al., "Importance of Conformational Variability in Protein Engineering of Subtillisin," ACS Symposium Series: 334, pp. 139–147 (1987).

Russell et al., "Electrostatic Effects on Modifiction of Charged Groups in the Active Site Cleft of Subtilisin by Protein Engineering," *J. Mol. Biol.*, vol. 193, No. 4, pp. 803–813 (1987).

Mandecki et al., "High–level expression of a gene encoding the human complement factor C5a in *Escherichia coli*," *Gene*, vol. 43, No. 1–2, pp. 131–138 (1986).

Brodin et al., "Expression of Bovine Intestinal Calcium Binding Protein from a Synthetic Gene in *Escherichia cole* and Characterization of the Product," *Biochemistry*, vol. 25, No. 10, pp. 5371–5377 (1986).

Hayashida et al., "Production and Characteristics of Raw–Starch–Digesting α–Amylase from a Protease–Negative *Asperigillus ficum* Mutant," *Appl. Environ. Microbiol.*, vol. 52, No. 5, pp. 1068–1073 (1986).

Upshall, "Filamentous Fungi in Biotechnology," *BioTechniques*, vol. 4, No. 2, 8 pages, (1986).

Esser et al., "Integrative Transformation of Filamentous Fungi with Respect to Biotechnological Application," *Process Biochemistry*, pp. 153–159 (1986).

Nakamura et al., "Stable Hyper–Production of *Escherichia coli* β–lactamase by *Bacillus subtilis* grown on a 0.5 M Succinate–Medium using a *b. subtilis* α–Amylase Secretion Vector," *Biochemical and Biophysical Research Communications*, vol. 128, No. 2, pp. 601–606 (1985).

Stepanov, "Fungal Aspartyl Proteinases," *Aspartyl Proteinases and their Inhibitors*, pp. 27–40 (1985).

Murao et al., "Pepstatin–Insensitive Acid Proteinases," *Aspartic Proteinases and their Inhibitors*, pp. 379–399 (1985).

Emmelo et al., "Controlled Synthesis of the Coat Protein of Satellite Tobacco Necrosis Virus in *Escherichia coli*," *Virology*, vol. 13, No. 1, pp. 32–40 (1984).

Kawamura et al., "Construction of a *Baccillus subtilis* Double Mutant Deficient in Extracellular Alkaline and Neutral Proteases," *J. Bacteriol.*, vol. 160, No. 1, pp. 442–444 (1984).

Hayashida et al., "Raw Starch–digestive Glucoamylase Productivity of Protease–less Mutant from *Aspergillus awamori* var. kawachi," *Agric Biol. Chem.*, vol. 45, No. 12, pp. 2675–2681 (1981).

Zubenko et al., "Protein Degradation, Meiosis and Sporulation in Proteinase–Deficient Mutants of *Saccharomyces Cerevisiae*," *Genetics*, vol. 97, pp. 45–64 (1981).

Kregar et al., "Proteases in Culture Filtrates of *Aspergillus Niger* and *Claviceps Purpurea*," *Struct. Funct. Appl. Aspects*, pp. 223–228 (1980).

A. Upshall et al. (1987) Biotechnology 5(12):1301–1304.

The Biotechnology of Filamentous Fungi, Chapter 6, Transformation, Eds. D.B. Finkelstein and C. Ball (1992) Butterworth & Heinenmann.

Bernard R. Glick and J.J. Pasternak (1989) Isolation, Characterization and Manipulation of Cellulase Genes, Biotechnol. Adv. 7(3):361–386.

J.L. Smith et al. (1991) Curr. Genet. 19:27–33.

R. Berka et al. (1989) Cloning of a Thermostable Glucoamylase from the Thermophilic Fungus *Humicola grisea* (var. thermoidea) and its Expression in *Aspergillus niger*. Development of a Transformation System for *H. grisea* and use of an Automated Screening Procedure for the Isolation of Mutants of *H. grisea* with Enhanced Glucoamylase Secretion, Presented at EMBO–Alko Workshop: Molecular Biology of Filamentous Fungi, Jul. 2–7, 1989, Espoo, Finland.

Y.M.J.T. de Ruiter–Jacobs, Curr. Genet. (1989) 16:159–163.

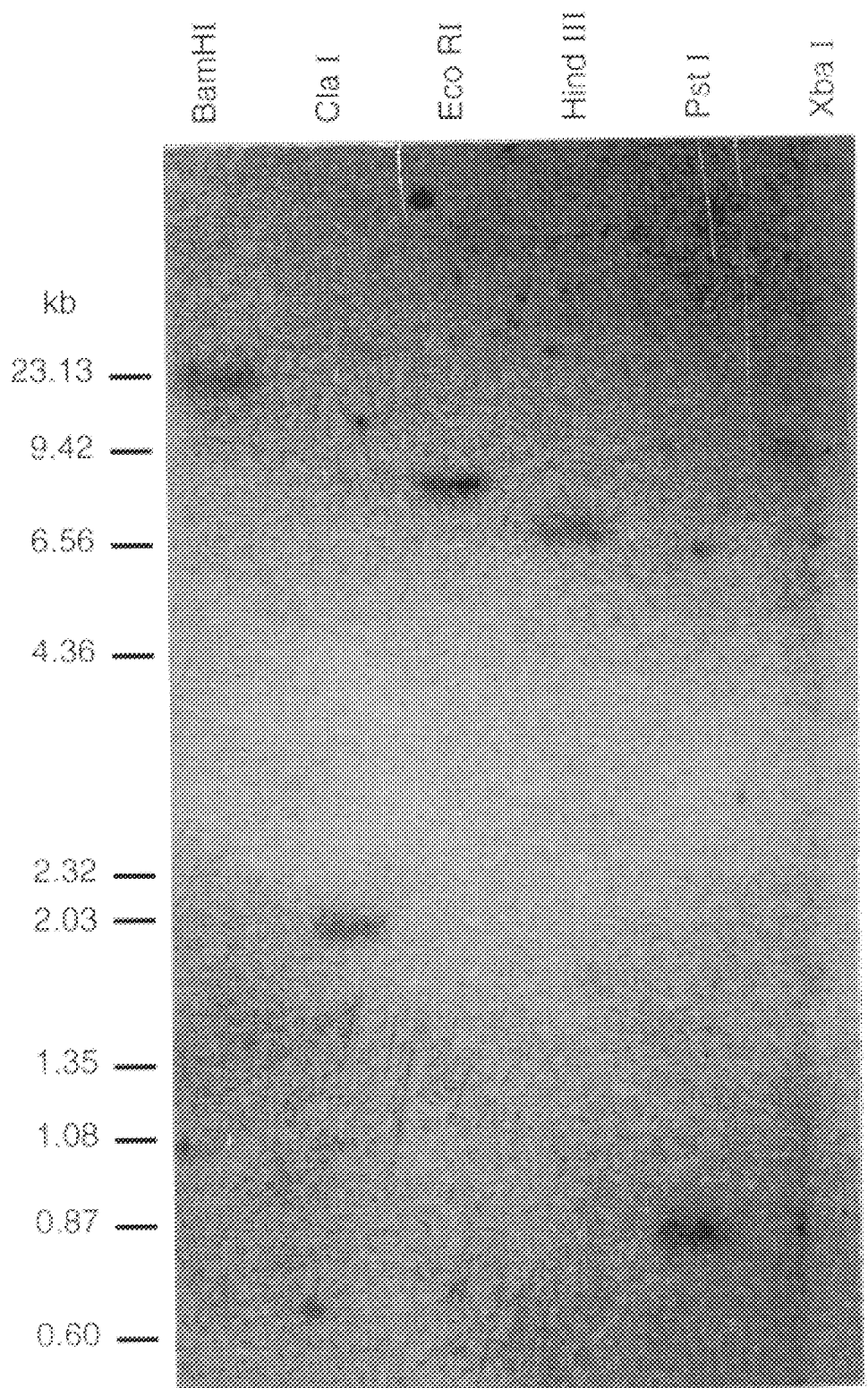
FIG._1

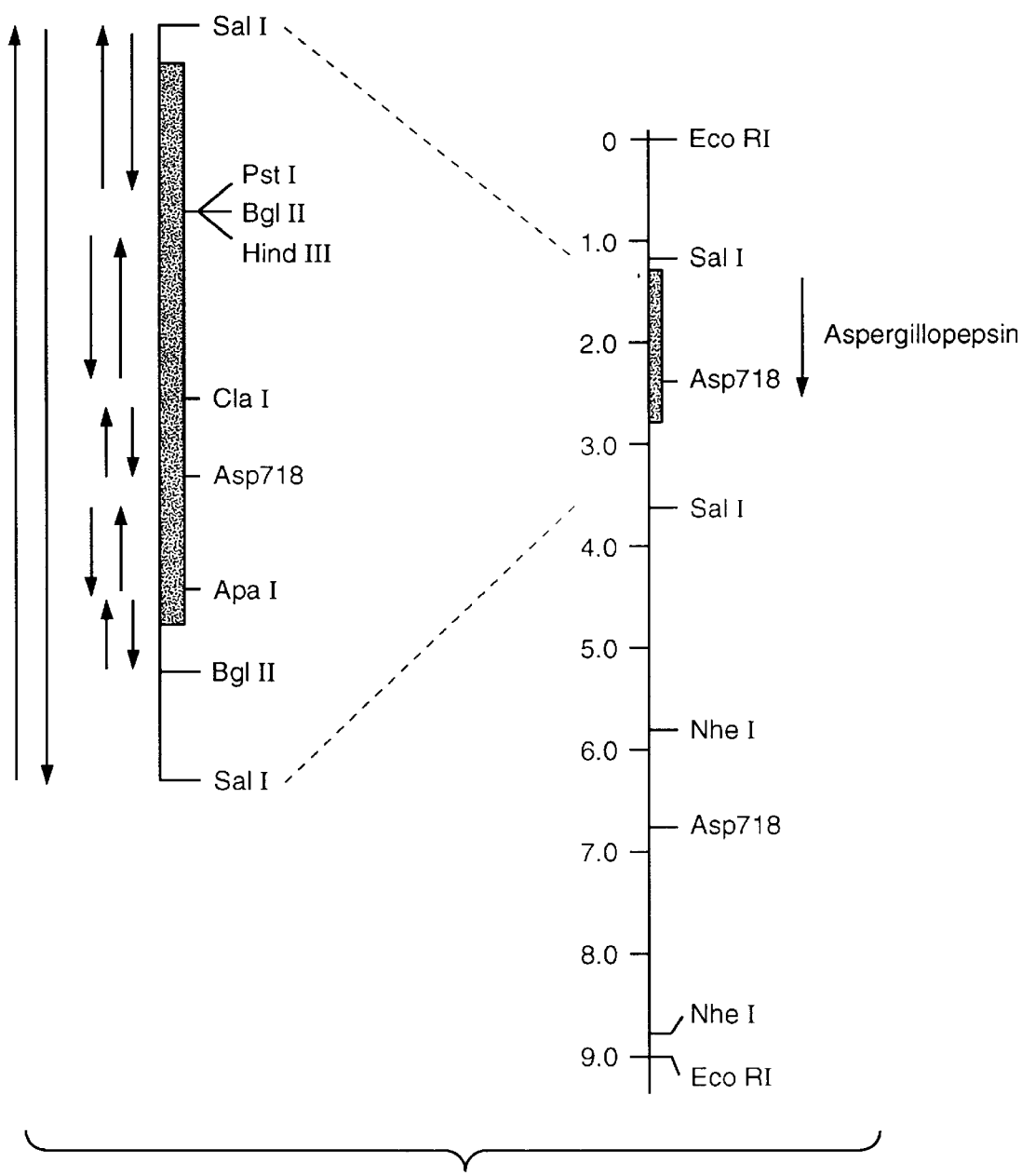
FIG._2

FIG._3A

```
  1 GTCGACTTGG ATGATGGAGG AGTTGATCGA GGTCAATGAG GAGAGGCTTG CAAGTATAAG

61 AAGAGACTGC TCGACCAGCA GAATGGATCT TCTTGTTCAT CAACCAAGAG TCCAAGGCTT

121 CTTTGTCTGG TTCTATCTCT TCTCCGAACT CTCTTGCTTG ACATTCTCGT GGTCAAA

178 ATG GTC GTC TTC AGC AAA ACC GCT GCC CTC GTT CTG GGT CTG TCC TCC
-69 Met Val Val Phe Ser Lys Thr Ala Ala Leu Val Leu Gly Leu Ser Ser

226 GCC GTC TCT GCG GCG CCG GCT ACT CCT CGC AAG GGC TTC ACC ATC AAC
-53 Ala Val Ser Ala Ala Pro Ala Thr Pro Arg Lys Gly Phe Thr Ile Asn

274 CAG ATT GCC CGG CCT GCC AAC CGC ACC AAG ATC AAC CTG CCA GGC
-37 Gln Ile Ala Arg Pro Ala Asn Arg Thr Lys Ile Asn Leu Pro Gly

322 ATG TAC GCC CGT TCC CTG GCC AAG TTT GGC GGT GTG CCC CAG AGC
-21 Met Tyr Ala Arg Ser Leu Ala Lys Phe Gly Gly Val Pro Gln Ser

370 GTG AAG GAG GAG GCT GCC AGC GGT AGT GCC ACG ACC CCC CAG AAC
 -5 Val Lys Glu Glu Ala Ala Ser Gly Ser Ala Thr Thr Pro Gln Asn

418 AAT GAC GAG TTT GAC CTG TAC CTC ACT CCC GTC ACT GTC GGA AAG TCC ACC CTC
 12 Asn Asp Glu Phe Asp Leu Tyr Leu Thr Pro Val Thr Val Gly Lys Ser Thr Leu

466 CAT CTG GAC TTT GAC ACC GGA TCT GCA GAT CT gta agcttccctg ctcgggt
 20 His Leu Asp Phe Asp Thr Gly Ser Ala Asp Le        u 518 gtt cgggcaaatc gtgactaacc tgactag  C TGG GTC TTC TCG GAC GAG CTC
 39                                      Trp Val Phe Ser Asp Glu Leu 570 CCT TCC TCG GAG CAG ACC GGT CAC GAT CTG TAC ACG CCT AGC TCC AGC
 46 Pro Ser Ser Glu Gln Thr Gly His Asp Leu Tyr Thr Pro Ser Ser Ser 618 GCG ACC AAG CTG AGC GGC TAC ATC TGG GAC TCC TAC GGT GAC GGC
 62 Ala Thr Lys Leu Ser Gly Tyr Ile Trp Asp Ser Tyr Gly Asp Gly
```

FIG._3B

```
666  AGC TCG GCC AGC GGA GAC GTG TAC CGG GAT ACT GTC ACT GTC GGC GGT
78   Ser Ser Ala Ser Gly Asp Val Tyr Arg Asp Thr Val Thr Val Gly Gly

714  GTC ACC ACC AAC AAG CAG GCT GTT GAA GCA GCC AAG ATC AGC TCC
94   Val Thr Thr Asn Lys Gln Ala Val Glu Ala Ala Lys Ile Ser Ser

762  GAG TTC GTT CAG AAC ACG GCC AAT GAC GGC CTT TTG GGA CTG GCC TTT
110  Glu Phe Val Gln Asn Thr Ala Asn Asp Gly Leu Leu Gly Leu Ala Phe

810  AGC TCC ATC AAC ACT G gtgag tcaatcctac atcagccggg ttgacctacc tgct
126  Ser Ser Ile Asn Thr V 865  gaccga tagacag                TC CAG CCA AAG GCG CAG ACA ACC TTC TTC GAC ACC
131                                al Gln Pro Lys Ala Gln Thr Thr Phe Phe Asp Thr 913  GTC AAG TCC CAG CTG GAC TCT CCC CTT TTC GCC GTG CAG CTG AAG CAC
143  Val Lys Ser Gln Leu Asp Ser Pro Leu Phe Ala Val Gln Leu Lys His 961  GAC GCC CCC GGT GTT TAC GAC TTT GGC TAC ATC GAT GAT TCC AAG TAC
159  Asp Ala Pro Gly Val Tyr Asp Phe Gly Tyr Ile Asp Asp Ser Lys Tyr 1009 ACC GGT TCT ATC ACC TAC ACG TAC AGT ATC GGT AGC TCC CAG GGT TAC TGG
175  Thr Gly Ser Ile Thr Tyr Thr Tyr Ser Ile Gly Ser Ser Gln Gly Tyr Trp 1057 GGC TTC AGC ACC GAC GGC TAC GCC GAT AGT ATC GGT GAC GGC AGC TCC AGC TCC
191  Gly Phe Ser Thr Asp Gly Tyr Ala Asp Ser Ile Gly Asp Gly Ser Ser Ser 1105 AGC GGC TTC AGC GCC ATT GCT G gtaa gaaccgcctt catttaacac acaacttg
207  Ser Gly Phe Ser Ala Ile Ala A 1159 tc cacctcttta ctaactagtg tatag   AC ACC GGT ACC ACC CTC ATC CTC
215                                   sp Thr Gly Thr Thr Leu Ile Leu 1209 CTC GAT GAC GAA ATC GTC TCC GCC TAC TAC GAG CAG GTT TCT GGC GCC
222  Leu Asp Asp Glu Ile Val Ser Ala Tyr Tyr Glu Gln Val Ser Gly Ala 1257 TCA GGA GAG ACG GAA GCC GGT TAC GTT TTC TCT TGC TCG ACC AAC
238  Ser Gly Glu Thr Glu Ala Gly Tyr Val Phe Ser Cys Ser Thr Asn
```

FIG._3C

```
1305 CCC CCT GAC TTC ACT GTC GTG ATT GGC GAC TAC AAG GCC GTT GTT CCG
 254 Pro Pro Asp Phe Thr Val Val Ile Gly Asp Tyr Lys Ala Val Val Pro

1353 GGC AAG TAC ATC AAC TAC GCT CCC ATC TCG ACT GGC AGC TCC ACC TGC
 270 Gly Lys Tyr Ile Asn Tyr Ala Pro Ile Ser Thr Gly Ser Ser Thr Cys

1401 TTT GGC GGT ATC CAG AGC AAC AGC GGT CTG GGA TCC ATC CTG GGT
 286 Phe Gly Gly Ile Gln Ser Asn Ser Gly Leu Gly Ser Ile Leu Gly

1449 GAT GTT TTC TTG AAG AGC TAC GTG TTC GTC TTC AAC TCT GAG GGC CCT
 302 Asp Val Phe Leu Lys Ser Tyr Val Phe Val Phe Asn Ser Glu Gly Pro

1497 AAG CTG GGA TTC GCC GCT CAG GCT TAG     ATTATCC ACTGAAGTGG AGTCTATGA
 318 Lys Leu Gly Phe Ala Ala Gln Ala ******

1550 T CTGCTGATTG ATCCCTCGAC GATGAACTAC ATGTGGAAAT GCATAGCAGA CGAGGGTG

1609 AT GGTGATGATG TTGATTTGAT GATGACCCGT ACATACTTGA TGAAGCTCGG TACATAT

1668 GCA ATGTGACTGT ATCTATGTGA TGATATATGT ATCATCTCAT AACTTTTGGC TATGAG

1727 TGCA GGATAACACT GAACCAGTAG TAGTACTTTC CACT
```

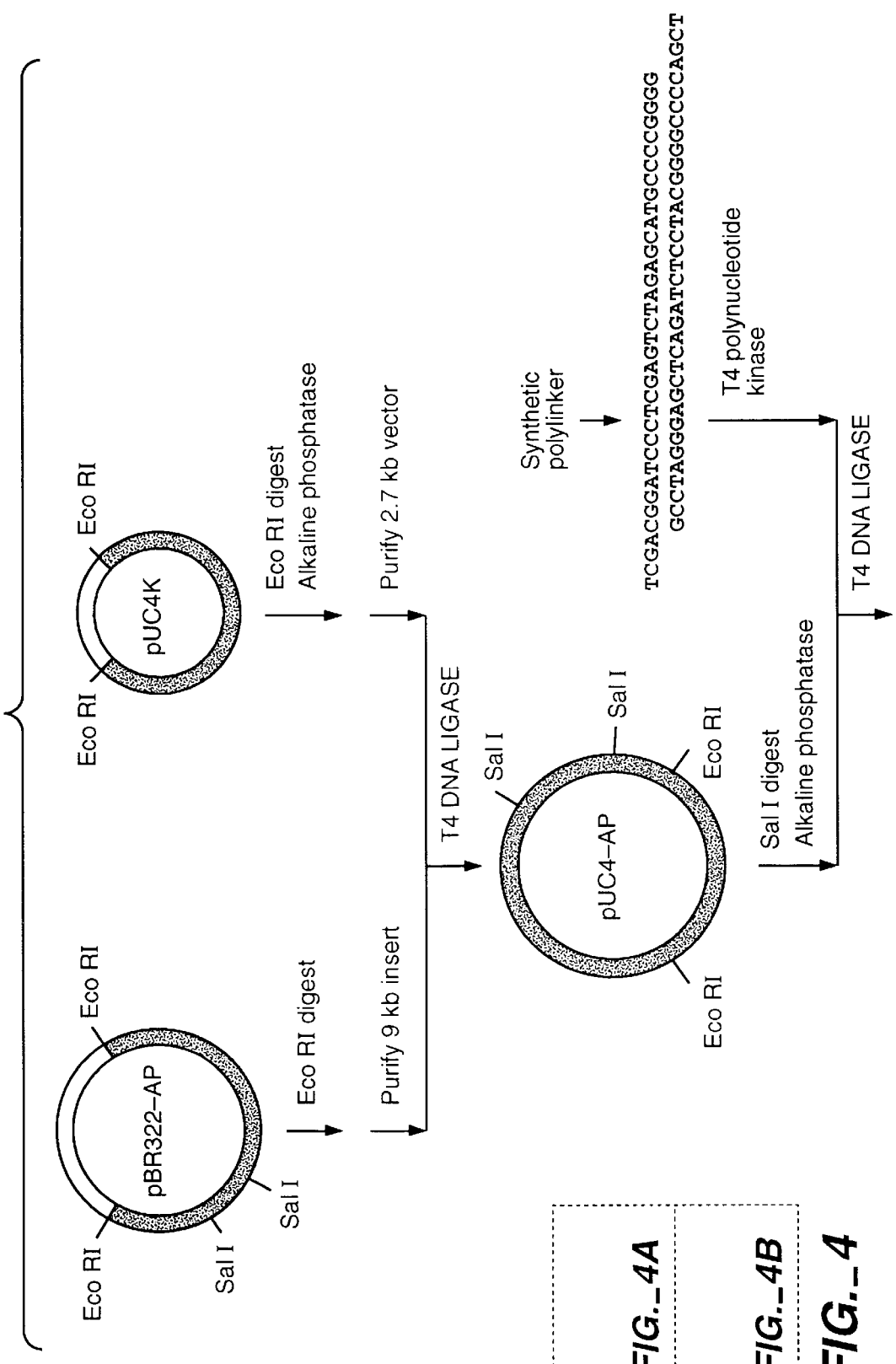

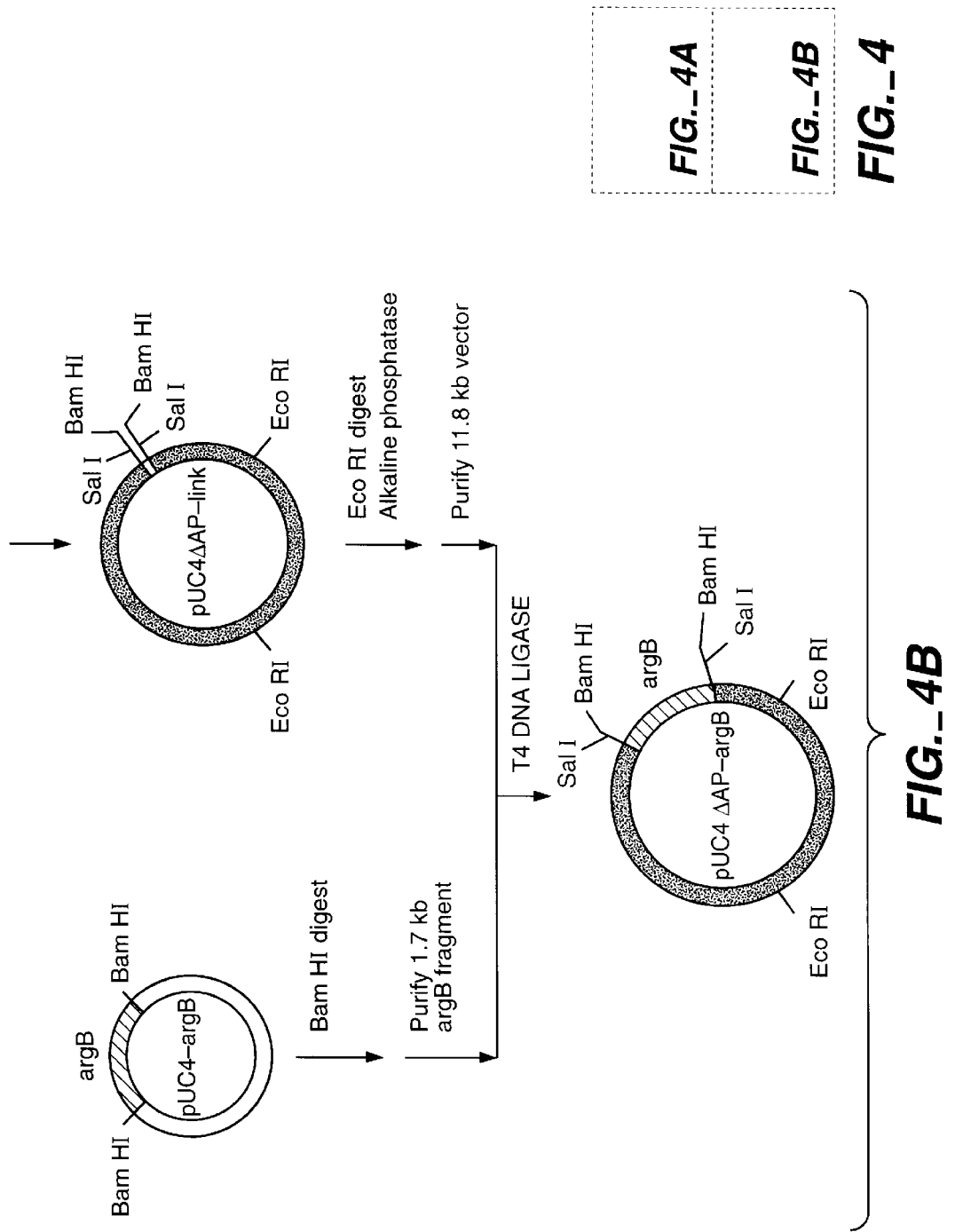
FIG._4B

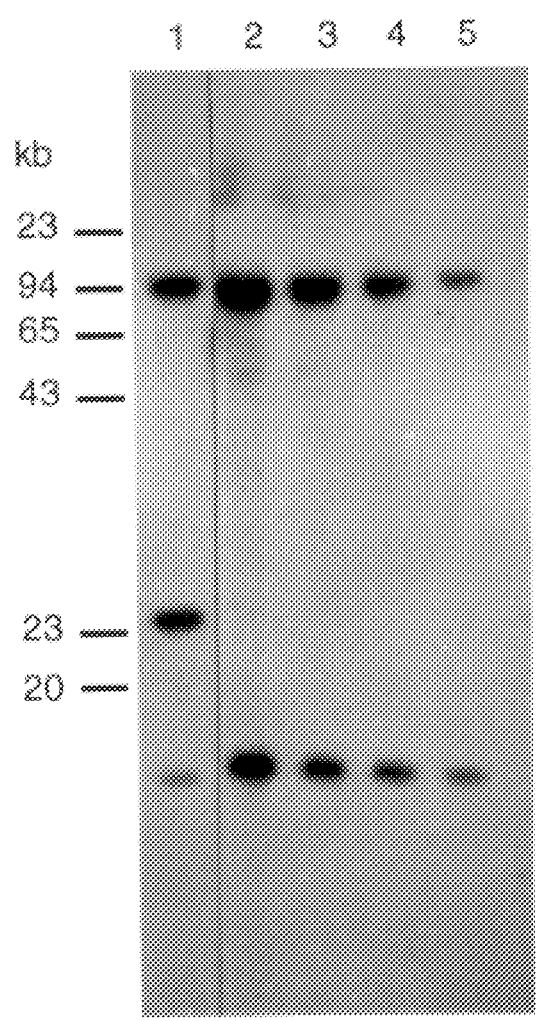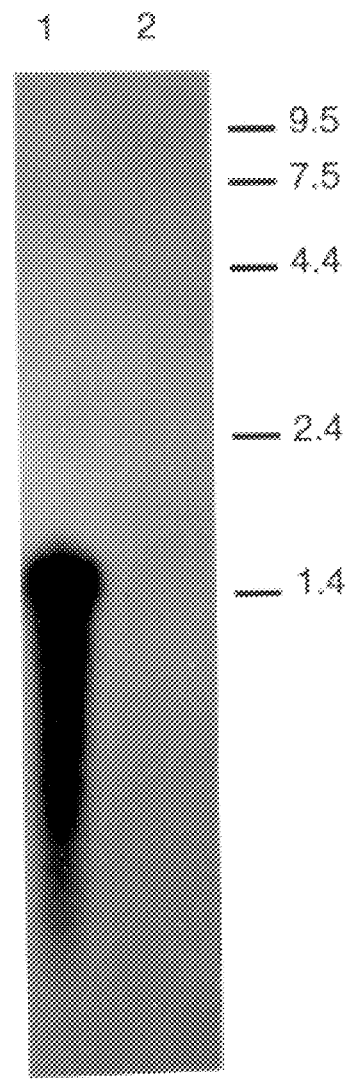
FIG._5A  FIG._5B

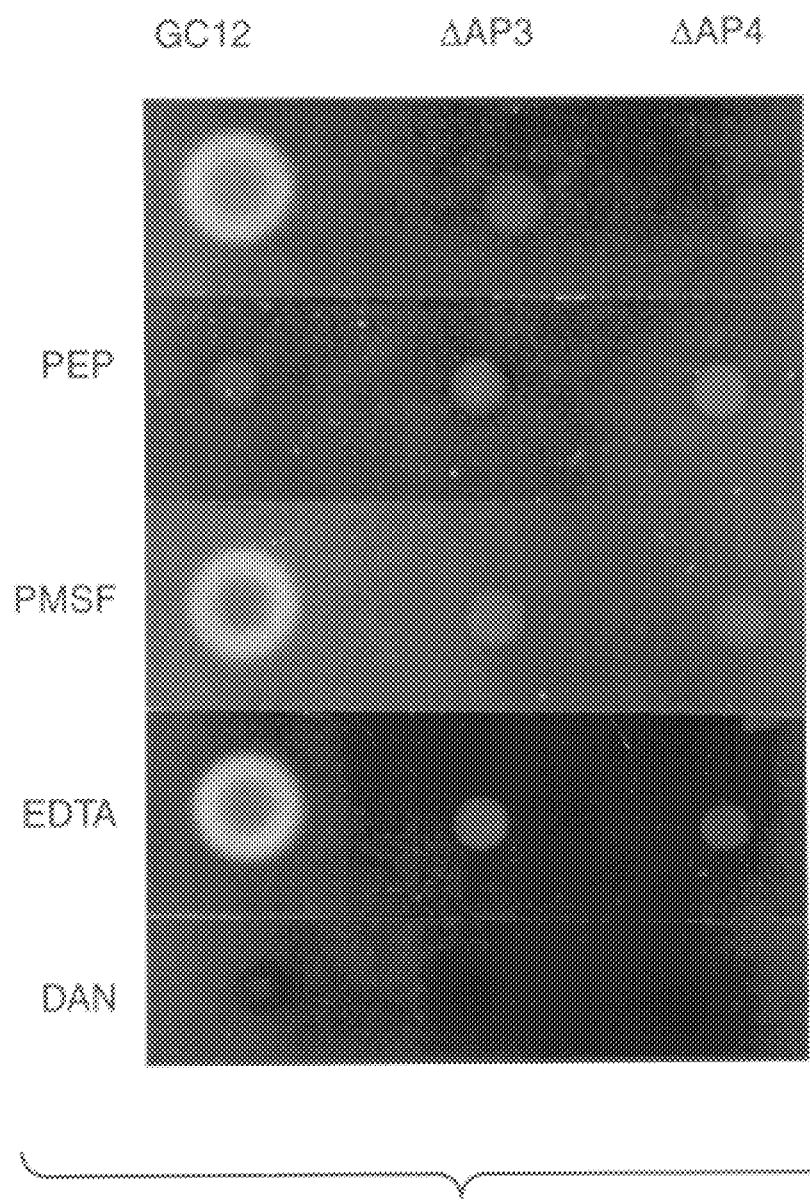
FIG._6

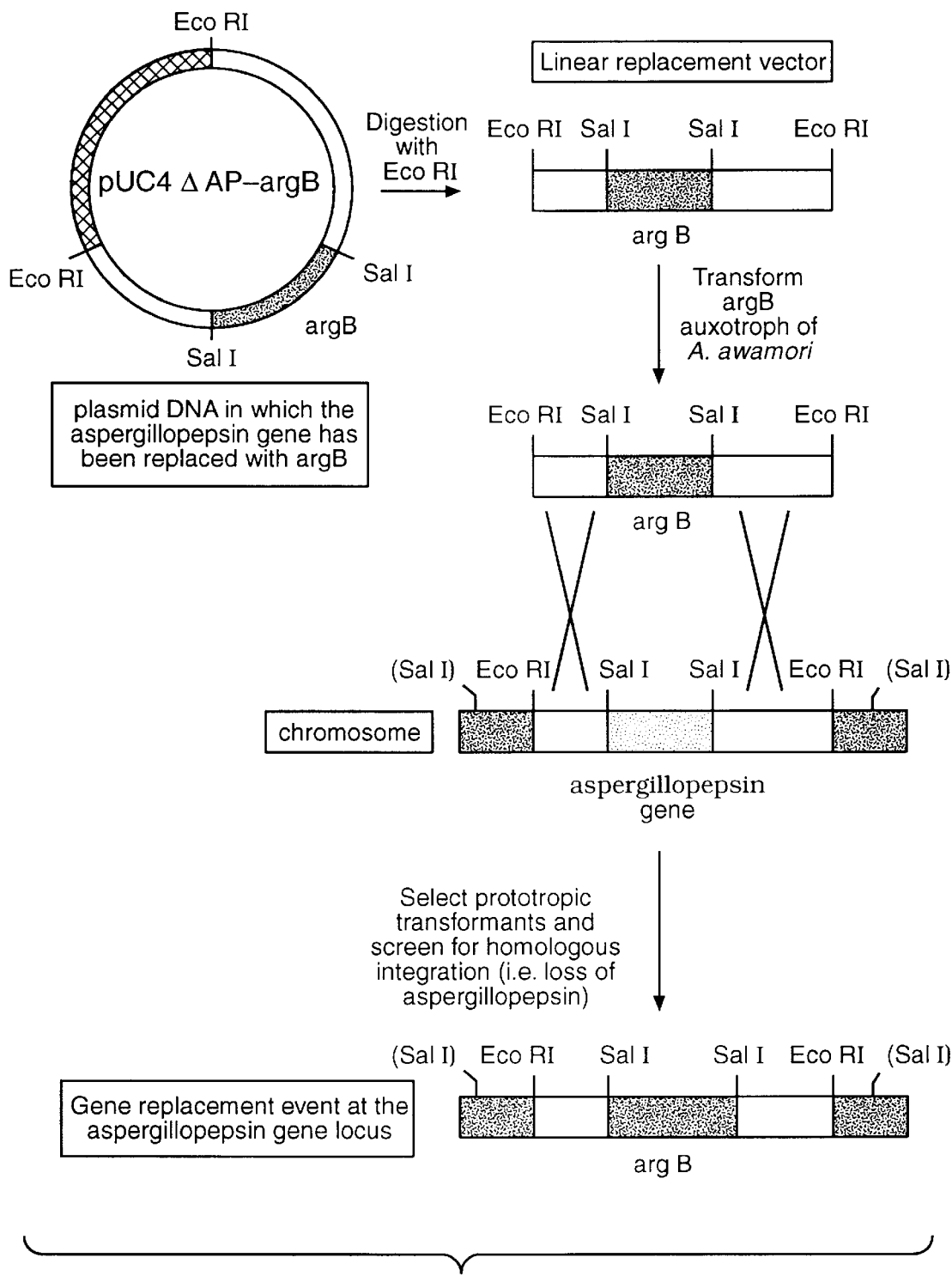
FIG._7

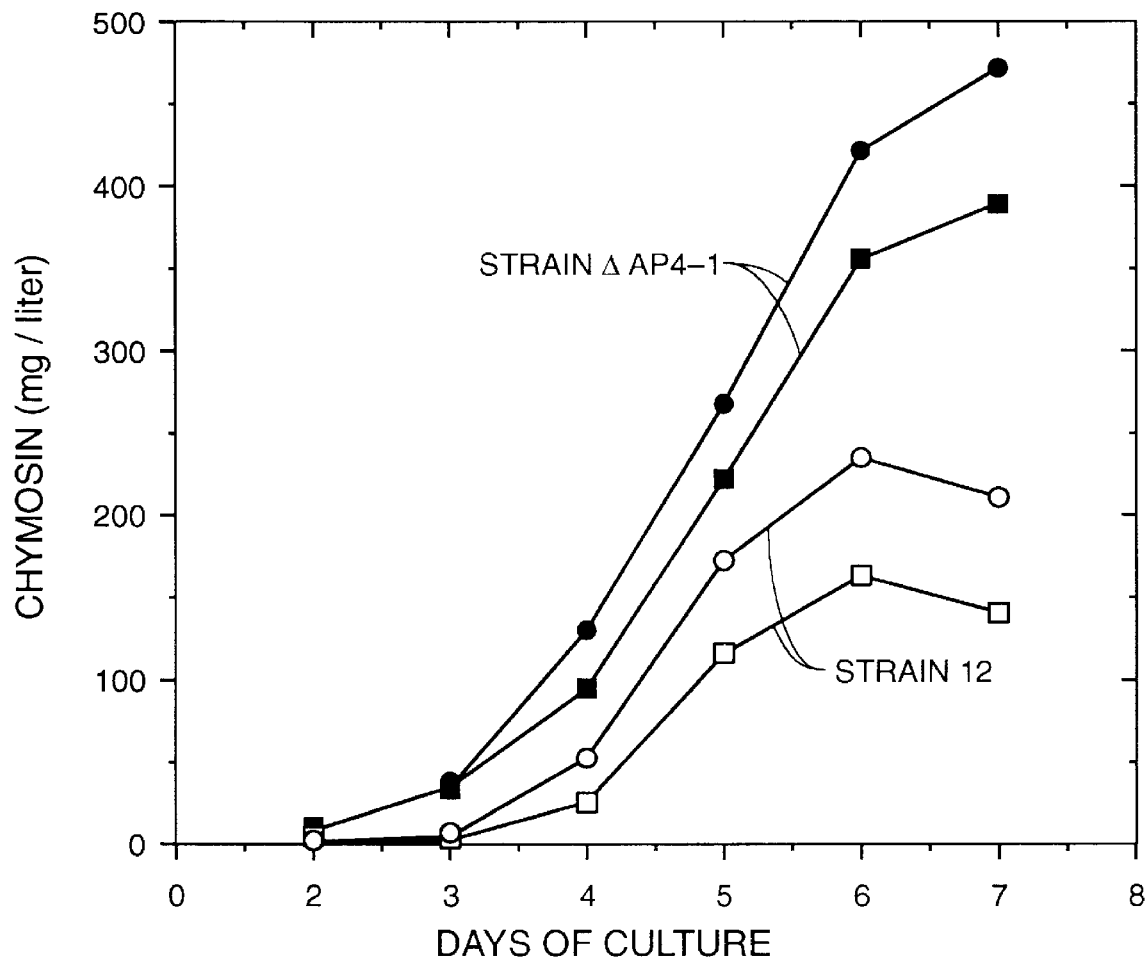
FIG._8

ASPARTIC PROTEINASE DEFICIENT FILAMENTOUS FUNGI

This is a Continuation of application Ser. No. 07/931,123 filed Aug. 17, 1992, abandoned, which is a Continuation of application Ser. No. 214,237 filed Jul. 1, 1988 now abandoned.

FIELD OF THE INVENTION

This invention relates to the production of polypeptides in suitable novel hosts. More particularly this invention relates to the production of heterologous polypeptides in novel filamentous fungal hosts which are incapable of excreting enzymatically active aspartic proteinase.

BACKGROUND OF THE INVENTION

The aspergillopepsins are a family of closely related aspartic proteinases produced by certain filamentous fungi of the genus Aspergillus. They share extensive amino acid sequence homology with the penicillopepsins, which are aspartic proteinases produced by certain Penicillium species, (In Kostka, V. (Ed.), "Aspartic Proteinases and Their Inhibitors", Walter de Gruyter, New York, pp. 27–40, 1985). The aspergillopepsins also share regions of homology with aspartic proteinases from other filamentous fungi such as Mucor miehei (Neth. Milk Dairy J., 35, pp. 275–280, 1981), Rhizopus chinensis (Can. J. Biochem., 51, pp. 789–796, 1973), and Endothia parasitica, (Eur. J. Biochem., 167, pp. 327–338, 1987). The degree of sequence conservation appears to be greatest in the regions surrounding active site amino acid residues.

The complete amino acid sequence of aspergillopepsin A from A. awamori has been reported (Bioorg. Khim., 8, pp. 1030–1047, 1986). The mature enzyme is composed of a single polypetide chain of 328 amino acids. Genes encoding the aspartic proteinases of Mucor miehei (Gene, 48, pp.41–53, 1986; Proteins 1, pp. 363–369, 1986), and Rhizopus chinensis (J. Biol. Chem., 262, pp. 1461–1467, 1987), have been cloned and their nucleotide sequences have provided information that these enzymes are synthesized as zymogen precursors. Fungal aspartic proteinases have been studied intensely and considerable information is available regarding the structure-function relationships (Biochim. Biophys. Acta, 336, pp. 437–444, 1974), as well as the three-dimensional structures of some of these enzymes (Nature, 267, pp. 808–813, 1977; Nature, 266, pp. 140–145, 1977; J. Mol. Biol., 196, pp. 877–900, FEBS Lett., 174, pp. 96–101, 1984; "Aspartic Proteinases and Their Inhibitors", Walter de Gruyter, New York, pp. 151–161 and 163–177, 1985).

Genomic DNA sequences encoding the Mucor miehei aspartic proteinase gene were isolated by Gray et al. (Gene, 48, pp. 41–53, 1986). The nucleotide sequence of this gene indicated that it contained no intervening sequences.

Filamentous fungi have recently been used as hosts for the expression and secretion of heterologous protein products (Bio/Technol., 5, pp. 369–376, 1987; Bio/Technol., 5, pp. 713–719, 1987; Bio/Techno., 5, pp. 1301–1304, 1987). While such aspartic acid proteinases from filamentous fungal hosts might degrade a heterologous polypeptide if left in contact with it for sufficient time, in vitro rapid separation of the protein has been thought to be sufficient to prevent any interference of aspartic proteinase with expression of the heterologous polypeptide expressed in filamentous fungi.

SUMMARY OF THE INVENTION

It has been discovered that when a filamentous fungus has the gene sequence corresponding to the aspartic proteinase produced therefrom inactivated or eliminated entirely by site specific DNA deletion in the gene sequence coding for the aspartic proteinase that such a fungus when used as a host for production of a heterologous polypeptide will surprisingly increase the production of the heterologous polypeptide produced thereby.

Accordingly, a novel mutant filamentous fungus and fungus culture is provided which is suitable for the production of heterologous polypeptides which contains a nonrevertable site-selected deletion that results in the filamentous fungus being incapable of excreting enzymatically active aspartic proteinase.

A method for producing a heterologous polypeptide in a filamentous fungus is described which comprises culturing a filamentous fungus which is capable of expressing the heterologous polypeptide and which contains a nonrevertable site-selected deletion that results in the filamentous fungus being incapable of excreting enzymatically active aspartic proteinase until an amount of the heterologous polypeptide has accumulated in the culture broth and then recovering the polypeptide.

BRIEF DESCRIPTION OF THE DRAWINGS

FIG. 1. Southern hybridization of total cellular DNA from A. awamori strain UVK143f. DNA was digested with the restriction enzymes indicated above each lane, fractionated by agarose gel electrophoresis, and blotted to Nytran membrane. The membrane filter was then probed with a radiolabeled 59mer corresponding to amino acid residues 5 through 24 of the mature aspergillopepsin A. Sizes of HindIII digested bacteriophage λ DNA markers and HaeIII digested φX174 RF-DNA markers are shown.

FIG. 2. Partial restriction map of a 9 kb EcoRI fragment and a 2.4 kb SalI fragment of A. awamori genomic DNA encoding the aspergillopepsin A gene. Directional arrows below the restriction map denote fragments that were subcloned into M13 vectors for DNA sequencing.

FIGS. 3A–3C. Nucleotide sequence of the aspergillopepsin A gene from A. awamori and the deduced amino acid sequence. Residues –69 through –50 comprise a putative signal peptide, and residues –49 through –1 may represent a highly charged propeptide region. A possible polyadenylation signal (***) is shown. The TATAA sequence upstream of the transcription initiation site is boxed. The consensus PuCTPuAC sequences, commonly found within introns of filamentous fungi are overlined.

FIGS. 4A–4B. Construction of the aspergillopepsin gene replacement vector pUCΔAP-argB. Details of this construction are outlined in the examples.

FIG. 5. PANEL A: Southern hybridization analysis of total cellular DNA extracted from aspergillopepsin-deficient transformants of A. awamori. The DNA was digested with SalI, fractionated by agarose gel electrophoresis and blotted to Nytran membrane. The membrane was probed with a radiolabeled fragment of A. awamori DNA containing the entire aspergillopepsin coding region as well as DNA sequences from the 5' and 3' flanking regions. Lanes, (1) strain GC12 control; (2) ΔAP3; (3) ΔAP4; (4) ΔAP5;(5) ΔAP6. The positions of HindIII digested bacteriophage λ DNA markers are shown. PANEL B: Hybridization analysis of total cellular RNA extracted from A. awamori strain UVK143f (lane 1), which is a wild-type control, and strain ΔAP6, which is an aspergillopepsin-deficient transformant. The positions of RNA size markers (Bethesda Research Laboratories, Gaithersburg, Md.) are shown.

FIG. 6. Aspergillopepsin activity in culture filtrates of strains GC12, ΔAP3, and ΔAP4 as detected on skim milk agarose plates. PEP, 0.1 mM pepstatin treated; PMSF, 1 mM phenylmethylsulfonyl fluoride treated; EDTA, 10 mM EDTA treated, DAN, 12 mM diazoacetylnorleucine methylester treated.

FIG. 7. Recombination model for the generation of aspergillopepsin-deficient strains of *A. awamori* by gene replacement events at the aspergillopepsin gene locus.

FIG. 8. Results from duplicate 50 ml shake flask cultures of an aspergillopepsin deleted strain (strain ΔAP4-1) and an aspergillopepsin non-deleted strain (strain 12). The concentration of chymosin was determined in surplus of supernatant taken from each culture every day, starting with day 2.

DETAILED DESCRIPTION OF THE INVENTION

Enzymatically active aspartic proteinases are those enzymes or pieces of enzymes which exhibit proteolytic activity at low pH and contain catalytic aspartic acid residues at their active site. They are normally isolated from filamentous fungi, are similar in activity and share regions of homology especially around active site amino acid residues. Where a great enough deletion occurs, i.e. where DNA encoding at least the 2 active site aspartic acid residues are excised from the gene sequence, such that any, if at all, polypeptide which is excreted is proteolytically inactive. Examples of aspartic proteinases are aspergillopepsin from Aspergillus, Mucor aspartic proteinase from Mucor, rhizopuspepsin from Rhizopus and endothiapepsin from Endothia.

Filamentous fungi suitable for the production of heterologous polypeptides refers to filamentous fungi which are or can be transformed or transfected with suitable vectors using recombinant DNA techniques. The term vectors refers to DNA constructs containing a DNA sequence which is operably linked to a suitable control sequence capable of effecting the expression of said DNA in a suitable host. Such control sequences include a promoter to effect transcription, an optional regulatory sequence to control such transcription, a sequence encoding suitable mRNA ribosome binding sites, and sequences which control termination of transcription and translation. The vector may be a plasmid, a virus particle, or simply a linear DNA fragment. Once transformed into a suitable host, the vector may integrate into the genome. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

"Incapable of excreting aspartic proteinase" means the organism is incapable of reversion to the wild type. Reversion is a finite probability over time that exists with naturally occuring or induced point mutations wherein the single mutations could easily naturally mutate back during production use to produce active gene product. This is to be contrasted with the large deletions or active site deletions provided herein. The deletions of the invention should be at least the codons for the 2 active site aspartic acid residues of the aspartyl proteinase gene sequence and preferably DNA encoding at least about 100 amino acids should be deleted. It is even more preferable that the entire gene sequence coding for the aspartic proteinase be deleted. It is possible to delete just the DNA encoding amino acids corresponding to the active site residues. In that case, it is most preferred that codons for at least 2 of the active site aspartic acid residues be deleted in order to prevent reversion to reconstruct an active form of enzyme. "Polypeptides" are polymers of amino acids which are covalently linked through peptide bonds. Polypeptides include low molecular weight polymers more commonly referred to as proteins. In addition, a polypeptide can be a phosphopolypeptide, glycopolypeptide or metallopolypeptide. Further, one or more polymer chains may be combined to form a polypeptide.

As used herein a "heterologous polypeptide" is a polypeptide which is not normally expressed and secreted by the filamentous fungus used to express that particular polypeptide. Heterologous polypeptides include polypeptides derived from prokaryotic sources (e.g., α-amylase from Bacillus species, alkaline protease from Bacillus species, and various hydrolytic enzymes from Pseudomonas, etc.), polypeptides derived from eukaryotic sources (e.g., bovine chymosin, human tissue plasminogen activator, human growth hormone, human interferon, urokinase, human serum albumin, factor VIII, etc.), and polypeptides derived from fungal sources other than the expression host (e.g., glucoamylase from *A. niger* and *Humicola grisea* expressed in *A. nidulans*, the aspartyl protease from *Mucor miehei* expressed in *A. nidulans*, etc.).

Heterologous polypeptides also include hybrid polypeptides which comprise a combination of partial or complete polypeptide sequences derived from at least two different polypeptides each of which may be homologous or heterologous with regard to the fungal expression host. Examples of such hybrid polypeptides include: 1) DNA sequences encoding prochymosin fused to DNA sequences encoding the *A. niger* or *A. awamori* glucoamylase signal and pro sequence alone or in conjunction with various amounts of amino-terminal or mature glucoamylase codons, and 2) DNA sequences encoding fungal glucoamylase or any fungal aspartic protease, human tissue plasminogen activator or human growth hormone fused to DNA sequences encoding a functional signal sequence alone or in conjunction with various amounts of amino-terminal propeptide codons or mature codons associated with the functional signal.

Further, the heterologous polypeptides of the present invention also include: 1) naturally occuring allelic variations that may exist or occur in the sequence of polypeptides derived from the above prokaryotic, eukaryotic and fungal sources as well as those used to form the above hybrid polypeptides, and 2) engineered variations in the above heterologous polypeptides brought about, for example, by way of site specific mutagenesis wherein various deletions, insertions or substitutions of one or more of the amino acids in the heterologous polypeptides are produced.

Each of the above defined heterologous polypeptides is encoded by a heterologous DNA sequence which contains a stop signal which is recognized by the filamentous fungus in which expression and secretion occurs. When recognized by those, the stop signal terminates translation of the m encoding the heterologous polypeptide.

The "filamentous fungi" of the present invention are eukaryotic microorganisms and include all filamentous forms of the subdivision Eumycotina. These fungi are characterized by a vegetative mycelium having a cell wall composed of chitin, cellulose, and other complex polysaccharides. The filamentous fungi of the present invention are morphologically, physiologically, and genetically distinct from yeasts. Vegetative growth of filamentous fungi is by hyphal elongation and carbon catabolism is obligately aerobic. In contrast, vegetative growth by yeasts such as *S. cerevisiae* is by budding of a unicellular thallus, and carbon catabolism may be fermentative. *S. cerevisiae* has a prominent, very stable diploid phase whereas, diploids exist only briefly prior to meiosis in filamentous fungi like *Aspergillus nidulans* and *Neurospora crassa*. *S. cervisiae* has 17 chromosomes as opposed to 8 and 7 for *A. nidulans* and *N. crassa* respectively. Recent illustrations of differences between *S. cerevisiae* and filamentous fungi include the inability of *S. cerevisiae* to process Aspergillus and Trichoderma introns and the inability to recognize many transcriptional regulators of filamentous fungi.

Various species of filamentous fungi may be used as expression hosts including the following genera: Aspergillus, Trichoderma, Neurospora, Podospora, Endothia, Mucor, Cochliobolus, and Pyricularia. Specific expression hosts include *A. nidulans, A. niger, A. awamori*, e.g., NRRL 3112, ATCC 22342 (NRRL 3112), ATCC 44733, ATCC 14331 and strain UVK143f, *A. oryzae*, e.g., ATCC 11490, *N. crassa* (16, 17, 23), *Trichoderma reesei*, e.g. NRRL 15709, ATCC 13631, 56764, 56765, 56466, 56767, and *Trichoderma viride*, e.g., ATCC 32098 and 32086.

As used herein, a "promoter sequence" is a DNA sequence which is recognized by the particular filamentous fungus for expression purposes. It is operably linked to a DNA sequence encoding the above defined polypeptides. Such linkage comprises positioning of the promoter with respect to the initiation codon of the DNA sequence encoding the signal sequence of the disclosed transformation vectors. The promoter sequence contains transcription and translation control sequences which mediate the expression of the signal sequence and heterologous polypeptide. Examples include the promoter from *A. niger* glucoamylase, the *mucor miehei* aspartyl protease and *A. niger* α-glucosidase, *Trichoderma reesei* cellobiohydrolase I, *A. nidulans* trpC and higher eukaryotic promoters such as the SV40 early promoter.

Likewise a "terminator sequence" is a DNA sequence which is recognized by the expression host to terminate transcription. It is operably linked to the 3' end of the DNA encoding the heterologous polypeptide to be expressed. Examples include the terminator from *A. nidulans* trpc, *A. niger* glucoamylase (39,48), *A. niger* α-amylase, and the *mucor miehei* aspartic protease, although any fungal terminator is likely to be functional in the present invention.

A "polyadenylation sequence" is a DNA sequence which when transcribed is recognized by the expression host to add polyadenosine residues to transcribed mRNA. It is operably linked to the 3' end of the mRNA encoding the heterologous polypeptide to be expressed. Examples include polyadenylation sequences from *A. nidulans* trpc, *A. niger* glucoamylase, *A. niger* α-amylase, and the *mucor miehei* aspartic protease. Any fungal polyadenylation sequence, however, is likely to be functional in the present invention.

A "signal sequence" is an amino acid sequence which when operably linked to the amino-terminus of a heterologous polypeptide permits the secretion of such heterologus polypeptide from the filamentous fungus. Such signal sequences may be the signal sequence normally associated with the heterologous polypeptide (i.e., a native signal sequence) or may be derived from other sources (i.e., a foreign signal sequence). Signal sequences are operably linked to a heterologous polypeptide either by utilizing a native signal sequence or by joining a DNA sequence encoding a foreign signal sequence to a DNA sequence encoding the heterologous polypeptide in the proper reading frame to permit translation of the signal sequence and heterologous polypeptide. Signal sequences useful in practicing the present invention include signals derived from bovine preprochymosin, *A. niger* glucoamylase, the *mucor miehei* aspartic protease and *Trichoderma reesei* cellulases. However, any signal sequence capable of permitting secretion of a heterologous polypeptide is contemplated by the present invention.

A "propeptide" or "pro sequence" is an amino acid sequence positioned at the amino terminus of a mature biologically active polypeptide. When so positioned the resultant polypeptide is called a zymogen. Zymogens, generally, are biologically inactive and can be converted to mature active polypeptides by catalytic or autocatalytic cleavage of the propeptide from the zymogen.

In a preferred embodiment, the selected host filamentous fungus is an Aspergillus which is transformed to express the heterologous polypeptide chymosin. Chymosin from filamentous fungal hosts is of particular value in the making of cheese. Isolated recombinant chymosin from filamentous fungal hosts is usually contaminated with several other proteinases and it is felt that aspartic proteinase would produce off flavor in cheese due to its indiscriminate hydrolysis.

The disclosed preferred embodiments are presented by way of example and are not intended to limit the scope of the invention. One skilled in the art based on the disclosure could easily substitute other filamentous fungi, heterologous polypeptides and processing conditions based on this disclosure.

GENERAL METHODS

A filamentous fungus is selected which is capable or already is expressing a heterologus gene, for example, those filamentous fungi in U.S. Ser. No. 882,224, filed Jul. 7, 1986, commonly assigned, and which expresses an aspartic proteinase.

"Transformation" is a process wherein a transformation vector is introduced into a filamentous fungus. The methods of transformation of the present invention have resulted in the stable integration of all or part of the transformation vector into the genome of the filamentous fungus. When referring to the heterologous polypeptide, self replicating extra-chromasomal transformation vectors are also contemplated. A method used for transformation is described in detail in the Preferred Embodiment Section.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. In general, about 1 microgram of plasmid or DNA fragment is used with about 1 unit of enzyme and about 20 microliters of buffer solution. Appropriate buffers and substrate amounts with particular restriction enzymes are specified by the manufacturer. Incubation times of about one hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme may be followed by bacterial alkaline phosphatase hydrolysis of the terminal 5' phosphates to prevent the two ends of a DNA fragment from forming a closed loop that would impede insertion of another DNA fragment at the restriction site upon ligation.

"Recovery" or "isolation" of a given fragment of DNA from a restriction digest means separation of the digest by polyacrylamide or agarose gel electrophoresis, identification of the fragment of interest, removal of the gel section containing the desired fragment, and separation of the DNA from the gel generally by electroelution.

"Ligation" refers to the process of forming phosphodiester bonds between two double-stranded nucleic acid fragments. Unless otherwise stated, ligation was accomplished using known buffers in conditions with one unit of T4 DNA ligase ("ligase") per 0.5 microgram of approximately equal molar amounts of the DNA fragments to be ligated.

"Oligonucleotides" are short length single or double stranded polydeoxynucleotides which were chemically synthesized and then purified on polyacrylamide gels.

The inventors have demonstrated that when at least a portion of the aspartic proteinase gene is removed from a filamentous fungi by site-directed mutagenesis or other in vitro methods such as removal of the gene segment by restriction enzyme digestion such that it is incapable of reverting back to wild type expression of the aspartic proteinase that such organism is a useful host in the production of heterologous polypeptides. The result of this invention is that the host filamentous fungus will produce more heterologous polypeptide than when the host is also providing active aspartic proteinase. One can speculate as to the mechanism of increased production, e.g. proteinases degrade the produced polypeptide. Likewise, aspartic proteinase may interact with the production or function of other polypeptides which are necessary for the production of heterologous proteins, or that there is more energy available to the organism because it doesn't expend energy in the making of the aspartic proteinase. Whatever the mechanism, it is suprising that such an organism would survive without aspartic proteinase or that such mechanisms would be significant enough to result in an improved yield of heterologous polypeptide. Also, since there are many other proteinases in filamentous fungi it is surprising that deleting aspartic proteinase alone would be sufficient to improve expression to any significant degree.

While site-directed mutagenesis can be used to modify particular amino acid residues e.g. for changing or deleting the DNA encoding the active site amino acids, in general, a vector containing a portion homologous to the desired filamentous fungal aspartic proteinase but incorporating a deletion in the aspartic proteinase gene is used to transform the host filamentous fungus to one which is incapable of secreting active aspartic proteinase. Viable transformants may be identified by screening for a selectable marker which is included in the vector or screening for lack of the proteinase activity.

a) Cloning of the aspartic proteinase.

The desired aspartic proteinase is first purified. The desired filamentous fungus is grown in a culture medium. Cells are normally grown with appropriate levels of carbon nitrogen and sulfur substrates. (e.g. glucose, $NaNO_3$ and $MgSO_4$) for 3–5 days at temperatures of around 28–37° C. with appropriate aeration to allow for accumulation of the aspartic proteinase. The mycelia are then removed by filtration or centrifugation. The remaining culture broth is then subjected to any desired method to separate the proteinase from the broth. It is preferred that multiple chromatography steps or affinity columns are used to achieve an aspartic proteinase preferably of at least 95% purity.

The purified proteinase is then subjected to sequencing. One preferred method is $NH_2$-terminal sequencing. Other methods include sequence analysis of peptide fragments derived by chemical or enzymatic cleavage of the aspartic proteinase. The aspartic proteinases are about 328 amino acids in length.

The sequence of the proteinase is then used to construct an oligonucleotide probe. This construction of the probe needs only to correspond to about 6–20 amino acids of the mature proteinase. However, it has been discovered that probes for the first 25 or so amino acids (5–24 in aspergillopepin) are preferrable and substantially reduce the time to construct an appropriate probe. This is because the published amino acid sequence of aspergillopepsin contains few, if any regions of six or more contiguous amino acids with very low codon degeneracy. The oligonucleotide probe is then used to clone the asparatic proteinase gene. The filamentous fungal genomic DNA is isolated and is digested with appropriate restriction enzymes. The fragments are then separated by electrophoresis in an agarose gel, blotted onto a filter and probed with the oligonucleotide probe prepared from the asparatic proteinase sequence by any standard method for such treatment. A fragment corresponding to the DNA segment identified by hybridization to the oligonucleotide probe is isolated. The isolated fragment is used to ligate to an appropriate vector (e.g. pBR322) and then transform a host e.g. *E. coli* 294 to produce DNA clones.

b) Location of the coding region for aspartic proteinase and deletion selection.

The location of the 5' and 3' ends of the aspartic proteinase can then be determined by a number of methods. For example, the DNA clone is subjected to hybridization with oligonucleotides to locate the 5' and 3' termini. Alternatively, the DNA sequence can be used to determine the location of the gene. (*Proc. Nat. Acad. Sci. USA*, 74, pp. 5463–5467, 1977).

Once the location of the gene is determined, a portion or all of the aspartic proteinase gene is selected for deletion. Either a segment of DNA encoding at least about 100 consecutive amino acids is decided on, or 2 codons corresponding to 2 of the amino acids characterized as the catalytic sites of which there are 3 in aspartic proteinase. These sites are at or near Asp 32 Ser 35 or Asp 215 (porcine pepsin numbering system) and correspond roughly in all pepsin-like aspartic proteinases from eukaryotic sources. It is preferred that the entire gene be deleted. It is even more preferred that the entire gene and about at least 200 base pairs on either side of the gene sequence be deleted.

c) Deleting of selected gene sequence and optional replacement with a selectable marker.

Once the gene sequence for deletion is determined any convenient method may be used to delete the gene sequence. Site-directed mutagenesis can be used to mutate single sites (e.g. where single deletions of active site amino acids is accomplished) or removal of the gene segment by use of restriction enzymes. Once the deletion is made, the remaining 5' and 3' ends are linked or preferably the deleted sequence is replaced by a sequence which is inactive (i.e.

does not encode an active proteinase enzyme). A preferred replacement sequence would contain a selectable marker to make identification of the later transformed mutants possible. Suitable selectable markers include arB, pyrG trpC or drug resistance markers such as hygromycin or bleomycin resistance genes. If a selectable marker is not used then it is possible to just screen transformant colonies by activity, or lack of it, of the desired proteinase enzyme.

d) Transformation of aspartic proteinase-producing filamentous fungi with mutated gene.

The mutant aspergillopepsin gene sequence is then incorporated into a wild type genome. A preferable method is homologous recombination where a linear DNA fragment comprising the mutant aspergillopepsin gene, containing a selectable marker for filamentous fungi (e.g. argB, pyrG), is used to transform a host fungus with an appropriate genetic background (e.g. argB or pyrG auxotrophs). By selective pressure for the marker contained on the mutant aspergillopepsin gene, approximately 20 percent of the resulting tranformants have arisen by a homologous integration event at the aspergillopepsin gene locus, and producing a genetic deletion of the aspergillopepsin (aspartic proteinase) gene. After transformation and purification the appropriate strain can be transformed to produce heterologous protein gene products such as chymosin by methods known in the art.

DESCRIPTION OF THE PREFERRED EMBODIMENT

We have cloned genomic DNA sequences encoding the aspergillopepsin A from *Aspergillus awamori* using a synthetic oligonucleotide probe. The nucleotide sequence of the gene revealed that the aspergillopepsin is encoded by four exons of 320, 278, 248, and 308 base pairs. Three introns, which interupt the coding sequence are 50, 52, and 59 base pairs in length. Directly downstream of the putative start codon lies a sequence encoding 69 amino acids which are not present in the mature aspergillopepsin protein. Based on similarities to other aspartic proteinases, this region may represent a 20 amino acid signal peptide followed by a 49 amino acid propetide that is rich in basic residues. Northern blots of total cellular RNA extracted from *A. awamori* cells indicate that the aspergillopepsin gene is transcribed as a single 1.4 kb mRNA. Mutants of *A. awamori* lacking the aspergillopepsin A structural gene were derived by the following gene replacement strategy: First, we constructed a plasmid in which a 2.4 kb SalI fragment containing the entire aspergillopepsin coding region was deleted from a 9 kb EcoRI genomic DNA clone and replaced by a synthetic DNA polylinker. Secondly, a selectable argB gene was inserted into the polylinker. Thirdly, the EcoRI fragment which contained the deleted aspergillopepsin gene and the argB marker was excised from the plasmid and used to transform an argB auxotroph of *A. awamori*. From 16-40% of the resulting prototrophic transformants were found to have an aspergillopepsin-deficient phenotype when screened with an immunoassay using antibodies specific for aspergillopepsin. Southern hybridization experiments confirmed that these mutants resulted from a gene replacement event at the aspergillopepsin gene locus.

EXAMPLES (a) Fungal Strains

*Aspergillus awamori* UVK143f, a glucoamylase hyperproducing mutant of strain NRRL 3112, was used as a source of genomic DNA for cloning experiments. For the isolation of aspergillopepsin-deficient mutants, *A. awamori* strain GC12 (argB3, pyrG5) was used. *A. awamori* strain GC12 was derived from strain UVK143f by parasexual crossing of the following two auxotrophic mutants: *A. awamori* GC5 (pyrG5) which is a uridine-requiring auxotroph isolated by selection on 5-fluoro-orotic acid, (*Mol. Gen. Genet.,* 206, pp. 71–75, 1987), following mutagenesis of UVK143f with ultraviolet light (this mutant is deficient in orotidine 5'-monophosphate decarboxylase); *A. awamori* GC3 (argB3) which is an arginine-requiring auxotroph isolated by filtration enrichment, (*Gene,* 37, pp. 207–214, 1985) following nitrosoguanidine mutagenesis of UVK143f (this mutant is specifically deficient in ornithine carbamoyl transferase).

(b) Bacterial Strains, Cloning Vectors, and Plasmids

*Escherichia coli* 294 (ATCC 31446) was used for construction of DNA libraries and for routine plasmid propagation. *E. coli* JM101, (*Nucl. Acids Res.,* 9, pp. 309–321, 1981) was used as the host for bacteriophage M13 sequencing vectors mp18, mp19, (Gene, 33, pp. 103–119, 1985), um30, and um31 (International Biotechnologies, Inc., New Haven, Conn.). Plasmids pBR322, (*Gene,* 2 pp. 95–113, 1977) and pUC4K (Vieira, J. and Messing, J., (*Gene,* 19, pp. 259–268, 1982) have been described previously. The plasmid pUC4-argB is composed of a 1.7 kb segment of *A. nidulans* genomic DNA encoding the ornithine carbamoyl transferase (argB) gene inserted into the cloning vector pUC4K. The argB gene segment was comprised of a 1714 base pair StuI restriction fragment excised from plasmid pBB116, *Gene,* 25, pp. 109–117, 1983) and ligated into SmaI-cleaved and dephosphorylated pUC4K.

(c) Purification of Aspergillopepsin and Amino Acid Sequencing

For production of aspergillopepsin *A. awamori* UVK143f was grown in a 4 liter culture flask containing one liter of the following culture medium: 6% soybean meal, 1.2% soy oil, and 0.6% $MgSO_4$. The medium was buffered at pH 4.5 with sodium phosphate. Mazu DF60-P (Mazur Chemicals, Inc., Gurnee, Ill.) was used as antifoam. The cells were grown for 4 days at 37° C. with vigorous aeration. The mycelia were removed by filtration through Miracloth (Cal-Biochem, LaJolla, Calif.) and the resulting filtrate was desalted on a 4.8 liter GF05 column (Reactifs IBF, Villeneuve la Garenne, France) equilibrated with 50 mM sodium acetate, pH 5.0. The material was then chromatographed on DEAE-trisacryl (Reactifs IBF) in 50 nM sodium acetate, pH 5.0. The aspergillopepsin was eluted at 250 mM NaCl in a linear gradient of 0–500 mM NaCl in the same buffer. The peak of aspergillopepsin activity (as determined by clotting activity on skim milk agarose) was pooled and applied to a gramicidin-S affinity column, *Bioorg. Khim.,* 3, pp. 831–835, 1977) in 50 mM sodium acetate at pH 4.5. The enzyme was then eluted with 1M NaCl and 10% isopropanol in the same buffer and immediately desalted by chromatography on a GF05 column equilibrated in 50 mM sodium acetate at pH 5.0. At this point, the aspergillopepsin was judged to be about 90–95% homogeneous based on silver-stained SDS-PAGE gels. The enzyme was stored at -70° C. Before further analysis, the aspergillopepsin preparation was chromatographed on an FPLC Mono-Q column (Pharmacia) in 50 mM sodium acetate, pH 5.0, using a linear gradient of 0–500 mM NaCl.

An aliquot of aspergillopepsin was heat denatured in the presence of 0.1 mM pepstatin. The protein was precipitated with 10% TCA and centrifuged at 7000×g for 10 minutes at 4° C. The pellet was washed once with acetone and solubilized in 8M urea, 50 mM Tris-HCl, pH 8.0. Dithiothreitol was added to 4 mM and the mixture was incubated for 10 minutes at room temperature. Iodoacetic acid (2M in 1M tris-base) was added to 13 mM and the mixture was incubated for 30 minutes at room temperature. The dithiothreitol concentration was raised to 8 mM and the mixture was incubated for another 10 minutes. The protein was TCA precipitated as above and the resulting pellet was dissolved in 8M urea, 50 mM Tris-TFA, pH 8.0. The protein solution was stored at −70° C. until needed.

A 2.5 nmol sample of the reduced and carboxymethylated aspergillopepsin preparation was subjected to $NH_2$-terminal sequencing on a multiphase protein sequenator (Dr. William Kohr, Genentech, Inc., South San Francisco, Calif.).

To another aliquot of aspergillopepsin, trypsin was added to 1% of the total protein and the mixture was incubated at 37° C. for one hour. An equal volume of HPLC solution A (0.05% TEA, 0.05% TFA in water) was added to stop the trypsin. The resulting fragments were separated by chromatography on a Brownlee C-2 column using a linear gradient of 0–100% HPLC solution B (0.05% TEA, 0.05% TFA in n-propanol) at a rate of 1% per minute. Three peaks were collected for amino acid sequencing as described above.

(d) Oligonucleotide Probes

The aspergillopepsin A amino acid sequence Ala-Val-Thr-Thr-Pro-Gln-Asn-Asn-Asp-Glu-Glu-Tyr-Leu-Thr-Pro-Val-Thr-Val-Gly-Lys, corresponding to residues 5 through 24 of the mature enzyme, was used to design the following 59 base pair synthetic oligonucleotide probe for cloning experiments:

5' dGCTGTGACCACCCCCCAGAACAACGAC-
GAGGAGTACCTGACCCCCGTGACCGTGGGCAA 3'

The nucleotide composition for this probe was based on the codon bias that exists for the *A. awamori* glucoamylase gene (Nunberg, J. H., Meade, J. H., Cole, G., Lawyer, F. C., McCabe, P., Schweickart, V., Tal, R., Whitman, V. P., Flatgaard, J. E., and Innis, M. A., *Mol. Cell. Biol.*, 4, pp. 2306–2315, 1984). The probe was synthesized by the triester method described by Crea et al. (Crea, R., Krasyewski, A., Hirose, T., and Itakura, K.: "Chemical synthesis of genes for human insulin", *Proc. Nat. Acad. Sci. USA,* 75, pp. 5765–5769, 1978).

(e) Isolation and Analysis of Nucleic Acids

*A. awamori* DNA and RNA were isolated as described previously, *Cell*, 26, pp. 29–37, 1981). Genomic DNA was digested with an appropriate restriction enzyme, fractionated on 1% agarose gels, and blotted to Nytran membranes (Schleicher & Schuell, Keene, N.H.). The membranes were probed for the presence of aspergillopepsin gene sequences by either of two methods. If the synthetic oligonucleotide described above was used as a probe, the following hybridization conditions were used: The membranes were incubated for one hour at 42° C. in the hybridization solution described by Adelman, J. P., Hayfick, J. S., Vasser, M., and Seeburg, P. H. (DNA, 2, pp. 183–193, 1983). Next, the oligonucleotide, which was radiolabeled with γ-[$^{32}$P]ATP (Amersham, Arlington Heights, Ill.) and T4 polynucleotide kinase (New England Biolabs, Beverly Mass.), was added to an activity of approximately $1\times10^6$ cpm/ml. The membranes were then incubated at 42° C. overnight with gentle agitation. The membranes were washed at 450° C. for 20 minutes in 0.5×SSPE with 0.1% SDS (Maniatis, T., Fritsh, E. F., and Sambrook, J.: "Molecular Cloning. A Laboratory Manual", Cold Spring Harbor Laboratory, Cold Spring Harbor, N.Y., 1982) followed by 30 minutes in 0.5×SSPE without SDS. Lastly, the membranes were dried, covered with plastic-wrap, and exposed to x-ray film (Kodak X-Omat) at −70° C. When using nick translated (Maniatis, T., Fritsh, E. F., and Sambrook, J.: "Molecular Cloning. A Laboratory Manual. Cold Spring Harbor Laboratory, Cold Spring Harbor, N.Y., 1982) restriction fragments as probes, the hybridization and washing conditions described by Davis, R. W., Botstein, D., and Roth, J. R. ("Advanced Bacterial Genetics", Cold Spring Harbor Laboratory, Cold Spring Harbor, N. Y., 1980) were used.

Total RNA from *A. awamori* cells was fractionated by formaldehyde-agarose gel electrohoresis (Davis, L. G., Dibner, M.D., and Battey, J. F.: "Basic Methods in Molecular Biology", Elsevier, N. Y., 1986) and blotted to Nytran membrane in 20×SSPE. Hybridization and washing conditions were the same as those described above for DNA hybridizations.

(f) Cloning of the Aspergillopepsin Gene

Southern blotting analysis of *A. awamori* genomic DNA revealed that the synthetic oligonucleotide probe described above hybridized to a single 9 kb EcoRI fragment (FIG. 1). Thus, the DNA was enriched for this fragment by isolating genomic fractions containing 6.5–9.5 kb EcoRI fragments using preparative agarose gel electrophoresis (Maniatis, T., Fritsh, E. F., and Sambrook, J.: "Molecular Cloning. A Laboratory Manual", Cold Spring Harbor Laboratory, Cold Spring Harbor, N.Y., 1982). The DNA from these fractions was electroeluted from the gel slices (Maniatis, T., Fritsh, E. F., and Sambrook, J.: "Molecular Cloning. A Laboratory Manual", Cold Spring Harbor Laboratory, Cold Spring Harbor, N.Y., 1982) and ligated to EcoRI cleaved and dephosphorylated pBR322. The ligation mixture was used in transformations of *E. coli* 294 and the transformants were screened for the presence of aspergillopepsin DNA sequences by the colony hybridization methods described by Davis, R. W., Botstein, D., and Roth, J. R. ("Advanced Bacterial Genetics", Cold Spring Harbor Laboratory, Cold Spring Harbor, N.Y., 1980). The filters were incubated with radiolabeled oligonucleotide probe under hybridization and washing conditions described above.

(g) Characterization of Aspergillopepsin Clones

Restriction mapping of apsergillopepsin clones was done as described previously (Maniatis, T., Fritsh, E. F., and Sambrook, J.: "Molecular Cloning. A Laboratory Manual", Cold Spring Harbor Laboratory, Cold Spring Harbor, N.Y., 1982). All restriction enzymes used were supplied by Boehringer Mannheim Biochemicals (Indianapolis, Ind.), New-England Biolabs (Beverly, Mass.), and Bethesda Research Laboratories (Gaithersburg, Md.), and they were used according to the instructions of the manufacturer.

DNA sequence analysis was done by the dideoxy chain termination method, (*Proc. Nat. Acad. Sci. USA,* 74, pp. 5463–5467, 1977).

(h) Construction of Gene Replacement Vector

Construction of the apsergillopepsin gene replacement vector pUC4ΔAP-argB is outlined in FIG. 2. Briefly, the 9 kb EcoRI fragment containing the genomic aspergillopepsin gene segment was first subcloned into pUC4K. Next, a 2.4 kb SalI fragment containing the entire aspergillopepsin gene was excised and replaced with the following 36 bp linker:

5'TCGACGGATCCCTCGAGTCTAGAGCATGCCCCGGGG    3'
3'    GCCTCGGGAGCTCAGATCTCGTACGGGGCCCCAGCT5'

This linker contains unique restriction sites for BamHI, XhoI, XbaI, SphI, and SmaI. Into the BamHi site of this linker a selectable argB gene from *A. nidulans* was inserted. The resulting plasmid, called pUC4ΔAP-argB, was cleaved with EcoRI and the linear fragment mixture was used to transform an arginine-requiring auxotroph of *A. awamori*.

(i) Transformation Procedure

Conidia of A. awamori strain GC12 were germinated by incubation in YEG medium (0.5% yeast extract, 2% glucose) supplemented with 100 mg/ml uridine, 100 mg/ml arginine, and 50 μg/ml streptomycin. Protoplasts were isolated according to, (Bio/Technol., 5, pp. 369–376. 1987), washed twice by centrifugation and resuspension in 0.7M KCl, and once in electroporation buffer (7 nM sodium phosphate buffer, pH 7.2, 1 mMMgSO4, 1.2M sorbitol). Aliquots of $2 \times 10^7$ protoplasts were finally resuspended in 0.8 ml of electroporation buffer in Gene Pulser cuvettes (Bio-Rad Laboratories, Richmond, Calif.) and kept on ice for 10 minutes. DNA in less than or equal to 20 μl of TE buffer (10 mM Tris-HCl, pH 7.4, 1 mM EDTA) was added just prior to delivery of the electric pulse. Electroporation was performed using a Bio-Rad Gene Pulser apparatus according to the directions of the manufacturer. A single pulse of 2125 V/cm using a 25 μFD capacitor was delivered. After 10 minutes of incubation on ice the protoplasts were added to molten Aspergillus minimal medium, (Mol. Gen. Genet., 154, pp. 311–318, 1973) with 2% agar, 100 mg/ml uridine, 50 μg/ml streptomycin and 1.2M sorbitol, and poured onto solid plates of the same medium. Transformants appeared as colonies on the surface of the medium after approximately five days of incubation at 37° C. Spores from individual colonies were transferred to plates of fresh medium.

(j) Analysis of Aspergillopepsin Deficient Mutants

Spores from individual transformants were inoculated into 1.2 ml of SCM (Aspergillus minimal medium with 2% malt extract, 0.5% yeast extract, 0.1% bacto-peptone, 100 mg/ml uridine, 100 mg/ml arginine, and 50 μg/ml streptomycin) and cultured in the wells of 24-well microtiter plates for four days. Media samples were assayed for aspergillopepsin using an enzyme-immunoassay (ELISA), (Methods Enzymol, 70, pp. 419–439, 1980) based on rabbit anti-aspergillopepsin antibodies. The absorbance at 490 nm was recorded after developing the color reaction due to horseradish peroxidase-conjugated goat anti-rabbit antibodies and used for comparative purposes. The absolute amount of aspergillopepsin was not determined.

To detect proteinase activity in culture filtrates, strains were grown for three days in 50 ml of liquid SCM. Filtrates were desalted on a Sephadex G-25 column (Pharmacia, Uppsala, Sweden) equilibrated with 0.5M sodium acetate, pH 5.5. Aliquots (3 μl) were placed on solidified 1% agarose containing 0.2M sodium acetate, pH 5.3, and 1% skim milk. When required, the samples were pretreated by adding the following reagents and incubating at room temperature for one hour: Pepstatin to a final concentration of 1 mM from a stock solution in dimethylsulfoxide (DMSO); PMSF to a concentration of 10 mM from a stock solution in ethanol; EDTA, pH 5.5, to a final concentration of 50 mM. Treatment of samples with DAN, (J. Biol. Chem., 241, pp. 4295–4297, 1966) required initial treatment with cupric sulfate at 10 mM for one hour followed by the addition of 12 mM DAN from a stock solution in ethanol, for one hour at room temperature.

RESULTS (a) Isolation of the Aspergillopepsin A Gene

Although the primary structure of aspergillopepsin A from A. awamori was published previously, (Bioorg. him, 8, pp. 1030–1047, 1986) there were several residues of the protein which needed clarification. Thus, we purified the enzyme from culture filtrates and determined the $NH_2$-terminal sequence and the amino acid sequence of three tryptic peptides (Table 1). All of these data are in close agreement with those of Ostoslavskaya et al. (Bioorg. Khim, 8, pp. 1030–1047, 1986). In order to clone the DNA sequences encoding aspergillopepsin A, we elected to employ a single long oligonucleotide, choosing the codons according to the usage observed in another A. awamori gene (glucoamylase). Consequently, a 59 bp oligonucleotide was synthesized corresponding to amino acid residues 5 through 24 of the mature aspergillopepsin. This oligonucleotide was radiolabeled and used to probe A. awamori genomic DNA for the presence of aspergillopepsin gene sequences. The results shown in FIG. 1 indicate that the 59 bp probe hybridized to a single fragment in each of several restriction enzyme digests of A. awamori genomic DNA. We estimated the aspergillopepsin gene to be approximately 1.2 kb in size, based on the mature polypeptide of 328 amino acids and assuming a signal peptide/propeptide of approximately 60–70 amino acids as seen with the corresponding Mucor miehei gene, (Gene, 48, pp. 41–53, 1986). Therefore, we reasoned that the 9 kb EcoRI fragment might have a high probability of containing the entire aspergillopepsin A gene.

Genomic DNA was digested with EcoRI and the 6.5–9.5 kb fragments were isolated by preparative agarose gel electrophoresis. These fragments were then ligated to EcoRI-cleaved and dephosphorylated pBR322, and the ligation mixture was used to transform competent E. coli 294 cells. The resulting transformant colonies were probed for the presence of aspergillopepsin DNA sequences by colony hybridization. Several colonies that showed strong hybridization signals were chosen for further analysis. All of these isolates were found to contain pBR322-derivatives with an identical 9 kb EcoRI insert. A partial restriction map of one of these clones is shown in FIG. 2. Subsequent mapping and hybridization experiments using the 59 bp oligonucleotide probe localized the aspergillopepsin gene to a 2.4 kb SalI segment that was contained within the 9 kb EcoRI fragment. A restriction map of this 2.4 kb SalI fragment is also shown in FIG. 2.

(b) Structure of the Aspergillopepsin A Gene

The nucleotide sequence and deduced amino acid sequence of the aspergillopepsin A gene from A. awamori is shown in FIG. 3. The coding region is comprised 1342 bp including three small introns of 50, 52, and 59 bp. These introns were assigned on the basis of the published amino acid sequence for aspergillopepsin A, (Bioorg. Khim, 8, pp. 1030–1047, 1986) and because of the following features consistently found in the intervening sequences of filamentous fungi (Gurr, S. J., Unkles, S. E., and Kinghorn, J. R. In Kinghorn, J. R. (Ed.), Gene Structure in Eukaryotic Microbes", IRL Press, Oxford, pp. 93–139, 1987): First, as observed in the A. awamori glucoamylase gene, (Mol. Cell. Biol., 4, pp. 2306–2315, 1984), all of the introns begin with the sequence GTA/G and end with C/TAG. Secondly, within each intron lies a consensus PuCTPuAC sequence, thought to be necessary for intron splicing (Gurr, S. J., Unkles, S. E., and Kinghorn, J. R. In Kinghorn, J. R. (Ed.), Gene Structure in Eukaryotic Microbes", IRL Press, Oxford, pp. 93–139, 1987). Interestingly, the third intron of the aspergillopepsin gene shares a region of perfect homology with the consensus TACTAAC internal sequence of Saccharomyces cerevisiae introns (Gurr, S. J., Unkles, S. E., and Kinghorn, J. R. In Kinghorn, J. R. (Ed.), Gene Structure in Eukaryotic Microbes", IRL Press, Oxford, pp. 93–139, 1987).

The 5'-untranslated region of the aspergillopepsin gene shows several landmarks that are typical of a lower eukaryotic promoter. For example, the sequence TATAA was found beginning at position −123, relative to the start codon. There are a number of highly expressed genes in filamentous fungi in which transcription starts from the second A residue in the sequence C/GAAC/G, (*EMBO J.*, 3, pp. 1581–1585, 1984); Gurr, S. J., Unkles, S. E., and Kinghorn, J. R. In Kinghorn, J. R. (Ed.), Gene Structure in Eukaryotic Microbes", IRL Press, Oxford, pp. 93–139, 1987). We found three such sequences in the 5'-untranslated region of the aspergillopepsin A gene, beginning at positions −83, −65, and −32, before the start codon. Interestingly, all of these elements are flanked on either side by a pyrimidine-rich CT-motif. The transcription initiation sites for a number of filamentous fungal genes appear in or immediately downstream from such CT-boxes (Gurr, S. J., Unkles, S. E., and Kinghorn, J. R. In Kinghorn, J. R. (Ed.), "Gene Structure in Eukaryotiac Microbes ", IRL Press, Oxford, pp. 93–139, 1987).

Translation of most fungal genes begins at the first ATG, and there is usually a consensus of DNA around the start codon. This consensus region includes the −3 position (relative to the start codon) which is most frequently (83%) an A residue (Gurr, S. J., Unkles, S. E., and Kinghorn, J. R. In Kinghorn, J. R. (Ed.), Gene Structure in Eukaryotic Microbes", IRL Press, Oxford, pp. 93–139, 1987). The −3 position upstream of the putative start codon for aspergillopepsin is also A.

The consensus sequence AAUAAA is thought to be involved in the polyadenylation of the 3'-terminus of eukaryotic mRNA. Although this sequence is not a necessary feature, a near approximation of the AAUAAA motif does appear in the 3'-flanking regions of several fungal genes (Gurr, S. J., Unkles, S. E., and Kinghorn, J. R. In Kinghorn, J. R. (Ed.), Gene Structure in Eukaryotic Microbes", IRL Press, Oxford, pp. 93–139, 1987). In this regard, the sequence ATGAA, found 48 bp downstream of the stop codon for aspergillopepsin, is a close approximation and may represent a possible polyadenylation signal. A similar abbreviation (AUAA) of the consensus polyadenylation signal is found 36 bp upstream of the poly-A addition site of *A. awamori* glucoamylase mRNA, (*Mol. Cell. Biol.*, 4, pp. 2306–2315, 1984). Interestingly, a conserved hexanucleotide, GAAAUG, found 11 bp downstream of the polyadenylation signal for glucoamylase mRNA is also seen 14 bp downstream of the putative aspergillopepsin polyadenylation signal. The actual site of poly-A addition for *A. awamori* glucoamylase mRNA occurs within the sequence GUAAU, located 26 bp downstream of the hexanucleotide GAAAUG, (*Mol. Cell. Biol.*, 4, pp. 2306–2315, 1984). A similar sequence, GUGAU, is found in the aspergillopepsin sequence 20 bp downstream of the hexanucleotide GAAAUG, and may represent a possible polyadenylation site.

By comparing the deduced amino acid sequence with the data derived by $NH_2$-terminal sequencing of aspergillopepsin A, we observed an open reading frame encoding 69 amino acid residues that were not present in the mature aspergillopepsin. Based on a comparison to other aspartic proteinases, we suggest that the first 20 residues comprise a signal peptide for secretion, and the remaining 49 residues represent a propeptide region that is rich in basic amino acids such as Lys and Arg (Foltmann, B. and Pederson, V. B. In Tang, J. (Ed.), Acid Proteases: Structure, Function and Biology", Plenum, N.Y., pp. 3–22, 1977; *Nuc. Acids Res.,* 10, pp. 2177–2187, 1982; *Gene,* 48, pp. 41–53, 1986; *J. Biol. Chem.,* 263, pp. 1382–1385, 1988). The signal peptide contains a positively charged Lys residue near the $NH_2$-terminal Met followed by 11 consecutive hydrophobic residues preceeding a potential cleavage site of Val-Ser-Ala (for a review of signal peptide cleavage sites, see Perlman, D. and Halvorson, H. O., *J. Mol. Biol.,* 167, pp. 391–409, 1983). The deduced and directly determined, (*Bioorg. Khim,* 8, pp. 1030–1047, 1986) primary sequence for the mature portion of aspergillopepsin differ at the following positions: (1) Gln not Arg at +51; (2) Asp-Leu not Asn-Val at +55–56; (3) Asp not Asn at +72, 77, 149, and 196; (4) Thr-Asn not Asn-Thr at +97–98; (5) Gln not Glu at +100, 188, and 316; (6) Glu not Gln at +103; (7) Asp-Asp for Asx-Asx at +171–172; (8) Asn-Pro not Ser-Thr at +194–195; (9) Five Ser not four at +204–208; (10) Residues +113–126 should read Val-Gln-Asn-Thr-Ala-Asn-Asp-Gly-Leu-Leu-Gly-Leu-Ala-Phe; (11) Ser-Ala-Tyr-Tyr-Glu-Gln not Leu-Asn-Gly-Ser-Gly at +229–234; (12) Ala-Ser-Gly-Glu-Thr-Glu not Gln-Asn-Gln-Glu-Ala-Asp at +238–243; (13) Ser not Asx at +250; (14) Asn not Thr at +254; (15) Val-Val not Gly-X at +260–261; (16) Val not Gly at +269; (17) Insert Gly between Pro-Lys at +271; (18) Insert Ile between Pro-Ser at +279; (19) No Asx after Ser at +280; (20) Gly not Pro at +282; (21) Two Ser not one at +284–285; (22) Asn not Asp at +314.

The codon bias exhibited by the aspergillopepsin A gene (Table 2) is similar to that observed for the *A. awamori* glucoamylase gene, (*Mol. Cell. Biol.,* 4, pp. 2306–2315, 1984). As seen in the highly expressed genes of *A. nidulans* and *Neurospora crassa,* a number of generalizations (Gurr, S. J., Unkles, S. E., and Kinghorn, J. R. In Kinghorn, J. R. (Ed.), Gene Structure in Eukaryotic Microbes", IRL Press, Oxford, pp. 93–139, 1987) hold for the codon usage pattern of aspergillopepsin. First, there is a marked preference (71.8%) for codons using a pyrimidine in the third position. When purines are used in the third position, G is preferred over A, with the exception of Gly codons, in which GGA is preferred over GGG. The same exception can be noted in the *A. awamori* glucoamylase gene, (*Mol. Cell. Biol.,* 4, pp. 2306–2315, 1984). Lastly, the AGU and AGC codons for Ser are seldom used.

Based on the deduced amino acid sequence, aspergillopepsin A shares 62% homology with penicillopepsin, 56% with endothiapepsin, 37% with rhizopuspepsin, and 29% with Mucor aspartic proteinase. In addition, limited homology is shared with mammalian aspartic proteinases, swine pepsin (32%) and bovine chymosin (28%).

(c) Isolation and Characterization of Aspergillopepsin-Deficient Mutants

In order to generate strains of *A. awamori* that were specifically deficient in the production of aspergillopepsin, we employed a gene replacement strategy similar to that described by, (*Mol. Cell. Biol.,* 5, pp. 1714–1721, 1985). First, we constructed a gene replacement vector, called pUC4ΔAP-argB, as shown in FIG. 4. Plasmid pUC4ΔAP-argB contains a selectable argB gene from *A. nidulans* which is inserted into the 9 kb genomic DNA clone in place of the aspergillopepsin coding region. This vector was linearized by digestion with EcoRI, and used to transform an argB auxotroph of *A. awamori.*

Twenty-four transformants were screened for an aspergillopepsin deficient phenotype with an ELISA, and ten of these transformants gave comparatively low values. Four of the transformants (designated ΔAP3, DAP4, ΔAP5, and ΔAP6), which had the lowest absorbance values for the screening assay, were chosen for further study. The ELISA values for strains that were deficient in aspergillopepsin synthesis did not drop to zero due to non-specific cross reaction between the antibodies and components of the culture supernatants. This cross reactivity could be visualized by Western blot analysis using the same anti-aspergillopepsin antibodies. Because of this cross reaction, absolute values for the concentration of aspergillopepsin in culture samples were not derived.

To investigate whether the apparent aspergillopepsin-deficient phenotype was the result of a gene disruption total, cellular DNA was extracted from transformants ΔAP3, ΔAP4, ΔAP5, ΔAP6, and strain GC12, digested with SalI, and fractionated by agarose gel electrophoresis. After blotting onto Nytran membrane filters, the DNA was hybridized with a radiolabeled probe consisting of the 9 kb EcoRI fragment of A. awamori DNA containing the aspergillopepsin A gene. This probe hybridized to three SalI fragments present in DNA from strain GC12 (FIG. 5, Panel A). These hybridization signals represent the 2.4 kb SalI fragment which contains the aspergillopepsin gene and two flanking DNA fragments. However, if the 2.4 kb SalI fragment in the genome of a given transformant had been replaced by the 1.7 kb fragment of A. nidulans DNA containing the argB gene, the probe would be expected to hybridize only to the two flanking DNA fragments. From the data shown in FIG. 5 (Panel A), it is apparent that the 2.4 kb SalI fragment of the aspergillopepsin gene was absent in all four of the transformants identified by the ELISA, demonstrating that the aspergillopepsin gene had been replaced by the argB gene. It is likely that some or all of the other transformants which gave low absorbance values in the ELISA had undergone the same gene replacement event. The frequency of gene replacement among transformants is, therefore, at least 16% and could be as high as 40%.

RNA isolated from transformant ΔAP6 and from strain UVK143f was separated by electrophoresis and analyzed by Northern blotting. Hybridization was performed with a radiolabeled 9 kb EcoRI fragment of A. awamori DNA containing the aspergillopepsin gene. As shown in FIG. 5 (Panel B), it is evident that the abundant aspergillopepsin-specific mRNA present in strain UVK143f could not be detected in the RNA from strain ΔAP6.

Samples were taken from 50 ml shake flask cultures of transformants ΔAP3, ΔAP4, and strain GC12 and spotted onto skim milk agarose plates. After incubation for six hours at 37° C., the resulting zones of coagulation were photographed (FIG. 6). Extensive milk clotting was induced by the GC12 culture filtrate, whereas, only slight clotting was observed with samples from either of the two transformants. The majority of the milk clotting activity of GC12 was inhibited by the inclusion of pepstatin in the medium, as would be expected for an aspartic proteinase, (J. Biol. Chem., 251, pp. 7095–7102, 1976), leaving residual proteolytic activity similar to that of strains ΔAP3 and ΔAP4. Neither the aspartic proteinase activity of GC12 nor the residual activity of strains ΔAP3 or ΔAP4 were inhibited by PMSF or EDTA. However, no proteolytic activity was observed with samples from strains ΔAP3 or ΔAP4 spotted onto milk plates at pH 6.8. The small amount of residual proteolytic activity produced by ΔAP3 and ΔAP4 presumably reflects the presence of one or more secreted proteinases other than the deleted aspergillopepsin. We found that although this additonal proteinase activity was not inhibited by pepstatin (FIG. 6) it was partially inhibited by diazoacetyl-DL-norleucine methylester (DAN), although some clearing was still observed. Thus, there may be a pepstatin-insensitive aspartyl proteinase present similar to that described in Scytalidium lignicolum (Murao, S. and Oda, K. In Kostka, V. (Ed.), Aspartic Proteinases and Their Inhibitors", Walter de Gruyter, New York, pp. 379–399, 1985).

Use of aspergillopepsin-deficient Mutants for the Production of a Heterologous Polypeptide—Bovine Chymosin To illustrate the advantages of using aspergillopepsin-deficient mutants, we compared the production of bovine chymosin in wild-type and in mutants of A. awamori that were specifically lacking the aspergillopepsin gene. The strains were transformed using a vector similar to those described by Cullen et al., (Bio/Technol, 5, pp. 369–376, 1987) in that transcriptional, translational, and secretory components of the glucoamylase gene were employed to derive chymosin expression and secretion. Individual transformants were then cultured in soy meal medium (6% soy bean meal, 0.1% $NaH_2PO_4$, 0.1% $MgSO_4$, 1.5% $(NH_4)_2SO_4$, 0.1% Tween 80, 0.2% Mazu, 7% sodium citrate pH 6.2, 15% maltose, 100 mg/ml uridine, 100 mg/ml arginine, 50 μg/ml streptomycin) at 37° C. for 7 days, and the level of extracellular chymosin was determined during the growth period using an activity assay.

The results shown in FIG. 8 clearly show that chymosin production is greater in a strain that is specifically lacking the aspergillopepsin gene. Note that by day 7 of culture the amount of chymosin in the strain 12 transformant of an aspergillopepsin producing strain was decreasing whereas it was still increasing in the aspergillopepsin deficient strain. (strain ΔAP4-1). These data suggest that less degradation of the chymosin is likely to occur in strains which are deficient in aspergillopepsin, and hence the yield of heterologous protein is greater.

To summarize, we have shown that production of a heterologous gene product such as bovine chymosin is improved by using a host strain that is deficient in the production of proteolytic enzymes (e.g. aspergillopepsin) that could degrade the heterologous product. Furthermore, proteolytic enzymes such as aspergillopepsin in a chymosin preparation could produce undesirable off-flavors in cheese by enzymatic digestion of milk proteins.

TABLE 1

Amino acid sequence of protions of aspergillopepsin A from A. awamori $NH_2$-terminus:
$H_2N$-SerLysGlySerAlaValThrThrProGlnAsnAsnAspGluGluTyr
Tryptic peptide I:
SerThrLeuHisLeuAspPheAspThrGlySerAlaAspLeuTrpValPheSerAspGluLeuPro
Tryptic peptide II:
TyrIleAsnTyrAlaPro
Tryptic peptide III:
HisAspAlaProGlyValTyrAspPheGlyTyrIleAspAspSerLysTyr

TABLE 2

Comparison of codon frequency between the glucoamylase and aspergillopepsin genes of A. awamori.

| Amino acid | Codons | Occurrence in glucoamylase | Occurrence in aspergilloepsin |
|---|---|---|---|
| Phe | UUU | 4 | 5 |
|  | UUC | 18 | 14 |
| Leu | UUA | 0 | 0 |
|  | UUG | 6 | 2 |
|  | CUU | 3 | 2 |
|  | CUC | 17 | 7 |
|  | CUA | 2 | 0 |
|  | CUG | 20 | 15 |
| Ile | AUU | 12 | 3 |
|  | AUC | 11 | 14 |
|  | AUA | 1 | 0 |
| Met | AUG | 3 | 2 |
| Val | GUU | 6 | 9 |
|  | GUC | 15 | 14 |
|  | GUA | 2 | 0 |
|  | GUG | 19 | 7 |
| Ser | UCU | 16 | 7 |
|  | UCC | 19 | 17 |
|  | UCA | 4 | 1 |
|  | UCG | 14 | 5 |
|  | AGU | 12 | 2 |
|  | AGC | 23 | 21 |
| Pro | CCU | 4 | 6 |
|  | CCC | 10 | 7 |
|  | CCA | 0 | 2 |
|  | CCG | 8 | 2 |
| Thr | ACU | 20 | 9 |
|  | ACC | 39 | 21 |
|  | ACA | 5 | 1 |
|  | ACG | 10 | 6 |
| Ala | GCU | 25 | 8 |
|  | GCC | 19 | 21 |
|  | GCA | 10 | 2 |
|  | GCG | 11 | 4 |
| Tyr | UAU | 6 | 0 |
|  | UAC | 21 | 19 |
| STOP | UAA | 0 | 0 |
|  | UAG | 1 | 1 |
|  | UGA | 0 | 0 |
| His | CAU | 0 | 1 |
|  | CAC | 4 | 2 |
| Gln | CAA | 4 | 0 |
|  | CAG | 13 | 15 |
| Asn | AAU | 6 | 2 |
|  | AAC | 19 | 11 |
| Lys | AAA | 0 | 1 |
|  | AAG | 13 | 17 |
| Asp | GAU | 21 | 8 |
|  | GAC | 23 | 19 |
| Glu | GAA | 9 | 3 |
|  | GAG | 17 | 9 |
| Cys | UGU | 3 | 0 |
|  | UGC | 7 | 2 |
| Trp | UGG | 19 | 3 |
| Arg | CGU | 4 | 1 |
|  | CGC | 7 | 2 |
|  | CGA | 4 | 0 |
|  | CGG | 3 | 2 |
|  | AGA | 1 | 0 |
|  | AGG | 1 | 0 |
| Gly | GGU | 14 | 15 |
|  | GGC | 22 | 19 |
|  | GGA | 7 | 16 |
|  | GGG | 4 | 0 |

We claim:

1. A viable mutant Aspergillus selected from the group consisting of A. niger, A. awamori, and A. oryzae suitable for the production of heterologous polypeptides, wherein the mutant comprises a site-selected deletion of part or all of nucleic acid coding for an aspergillopepsin such that said mutant does not excrete said aspergillopepsin and does not revert to wild type, wherein said nucleic acid coding for said aspergillopepsin hybridizes to an oligonucleotide probe coding for six or more contiguous amino acids of the amino acid sequence of aspergillopepsin A from A. awamori.

2. The mutant according to claim 1 comprising DNA encoding a selectable marker at the site of the selected deletion.

3. The mutant according to claim 2 wherein the selectable marker is argB.

4. The mutant according to claim 1 wherein the site selected deletion excises DNA encoding at least 2 active site amino acids of the aspergillopepsin.

5. The mutant according to claim 1 wherein the site selected deletion of excises DNA encoding a continuous sequence of the aspergillopepsin at least about 100 amino acids long.

6. The mutant according to claim 1 which is A. niger.

7. The mutant according to claim 1 which is A. oryzae.

8. The mutant according to claim 1 which is A. awamori.

9. The mutant according to claim 1 further comprising a gene coding for the expression of a heterologous polypeptide such that the mutant produces the heterologous polypeptide.

10. The mutant according to claim 9 wherein the heterologous polypeptide is selected from the group consisting of tissue plasminogen activator, bovine chymosin, human serum albumin and mammalian growth hormone.

* * * * *